United States Patent [19]

Sytkowski et al.

[11] Patent Number: 5,614,184
[45] Date of Patent: Mar. 25, 1997

[54] RECOMBINANT HUMAN ERYTHROPOIETIN MUTANTS AND THERAPEUTIC METHODS EMPLOYING THEM

[75] Inventors: Arthur J. Sytkowski, Arlington, Mass.; Jennifer Grodberg, Montreal, Canada

[73] Assignee: New England Deaconess Hospital, Boston, Mass.

[21] Appl. No.: 383,743

[22] Filed: Feb. 2, 1995

Related U.S. Application Data

[63] Continuation-in-part of Ser. No. 113,080, Aug. 26, 1993, abandoned, which is a continuation-in-part of Ser. No. 920,810, Jul. 28, 1992, abandoned.

[51] Int. Cl.[6] .................. C07K 14/505; C12N 15/19; A61K 38/18; A61K 38/19
[52] U.S. Cl. .................. 424/85.1; 530/351; 530/397; 536/23.5; 536/23.51; 435/69.5; 514/8
[58] Field of Search .................. 530/351, 397; 536/23.5, 23.51; 435/69.5, 320.1, 240.2; 424/85.1; 514/8

[56] References Cited

U.S. PATENT DOCUMENTS

| | | | |
|---|---|---|---|
| 4,677,195 | 6/1987 | Hewick et al. | 514/8 |
| 4,703,008 | 10/1987 | Lin | 435/240.2 |
| 4,732,889 | 3/1988 | Cynshi et al. | 514/8 |
| 4,745,099 | 5/1988 | Akamatsu et al. | 514/8 |
| 4,835,260 | 5/1989 | Shoemaker | 530/397 |
| 4,954,437 | 9/1990 | Beck et al. | 435/69.4 |

FOREIGN PATENT DOCUMENTS

| | | |
|---|---|---|
| 2021528 | 7/1990 | Canada . |
| 0409113 | 1/1991 | European Pat. Off. . |
| WO91/05867 | 5/1991 | WIPO . |
| WO92/21029 | 11/1992 | WIPO . |
| WO94/24160 | 10/1994 | WIPO . |
| WO94/25055 | 11/1994 | WIPO . |

OTHER PUBLICATIONS

Krystal, G., "A Simple Microassay for Erythropoietin Based on [3]H-Thymidine Incorporation into Spleen Cells from Phenylhydrazine Treated Mice," *Exp. Hematol.*, 11(7): 649–660 (1983).

Jacobs, K., et al., "Isolation and Characterization of Genomic and cDNA clones of Human Erythropoietin," *Nature*, 313: 806–810 (1985).

Sytkowski, A.J., et al., "Isolation and Characterization of an Anti–peptide Monoclonal Antibody to Human Erythropoietin," *J. of Biol. Chem.*, 260(27): 14727–14731 (1985).

Sytkowski A.J., et al., "Immunochemical Studies of Human Erythropoietin Using Site–Specific Anti–Peptide Antibodies," *J. of Biol. Chem.*, 262(3): 1161–1165 (1987).

Wognum, A.W., et al., "Use of a Sensitive Bioimmunoabsorbent Assay to Isolate and Characterize Monoclonal Antibodies to Biologically Active Human Erythropoietin," *Blood*, 71(6): 1731–1737 (1988).

Dube, S., et al., "Glycosylation at Specific Sites of Erythropoietin is Essential for Biosynthesis, Secretion, & Biological Function," *J. of Biol. Chem.*, 263(33): 17516–17521 (1988).

Boissel, J.P., et al., "Erythropoietin Structure–Function Relationships," In *The Biology of Hematopoisis*, N. Dainiak et al., eds. (NY: Wiley–Liss, Inc.), pp. 227–232 (1990).

Yoshimura, A., et al., "Friend Spleen Focus–Forming Virus Glycoprotein gp55 Interacts With the Erythropoietin Receptor in the Endoplasmic Reticulum and Affects Receptor Metabolism," *Proc. Natl. Acad. Sci USA*, 87: 4139–4143 (1990).

Chern. J., et al., "Erythropoietin Activates the Receptor in Both Rauscher & Friend Murine Erythroleukemia Cells," *J. of Biol. Chem.*, 266(4): 2009–2012 (1991).

Watowich, S.S., et al., "Homodimerization and Constitutive Activation of the Erythropoietin Receptor," *Proc. Natl. Acad. Sci. USA*, 89: 2140–2144 (1992).

Fibi, M.R., et al., "Evidence for the Location of the Receptor–Binding Site of Human Erythropoietin at the Carboxyl–Terminal Domain," *Blood*, 77(6): 1203–1210 (1991).

Grodberg, J., et al., "Defining Human Erythropoietin Hormone Receptor Interactions by Site–Directed Mutagenesis," *Exp. Hematol.*, 20(6): 755 (Abstract 195) (Jul. 1992).

Higuchi, M., et al., "Role of Sugar Chains in the Expression of the Biological Activity of Human Erythropoietin," *J. of Biol. Chem.*, 267(11): 7703–7709 (1992).

Patel, H.R., et al., "Erythropoietin Causes Changes in Early Response Gene Expression Via Multiple Signaling Pathways: Distinct Roles for Protein Kinases & Phosphatases," *Blood*, 78(10): 304a (Abstract 1205) (Nov. 15, 1991).

Spangler, R., et al., "Erythropoietin Increases c–myc mRNA by a Protein Kinase C–dependent Pathway," *J. Biol. Chem.*, 266(2): 681–684 (1991).

Chern, Y., et al, "Structural Role of Amino Acids 99–110 in Recombinant Human Erythropoietin," *Eur. J. Biochem.*, 202: 225–229 (1991).

Yamaguchi, K., et al., "Effects of Site–Directed Removal of N–Glycosylation Sites in Human Erythropoietin on Its Production & Biological Properties," *J. Biol. Chem.*, 266(30): 20434–20439 (1991).

McDonald, J.D., et al., "Cloning Sequencing and Evolutionary Analysis of the Mouse Erythropoietin Gene," *Mol. and Cell Biol.*, 6(3): 842–848 (1986).

Boissel, J–P., et al., "Erythropoietin Structure–Function Relationships. Mutant Proteins that Test a Model of Tertiary Structure," *J. Biol. Chem.* 268(21): 15983–15993 (1993).

(List continued on next page.)

*Primary Examiner*—David L. Fitzgerald
*Attorney, Agent, or Firm*—Hamilton, Brook, Smith & Reynolds, P.C.

[57] ABSTRACT

DNA encoding modified, secretable erythropoietin proteins whose ability to regulate the growth and differentiation of red blood cell progenitors are different from the wildtype recombinant erythropoietin and to methods of modifying or altering the regulating activity of a secretable erythropoietin and using modified secretable erythropoietin proteins.

28 Claims, 13 Drawing Sheets

OTHER PUBLICATIONS

Grodberg, J., et al., "Characterizing Arginine 103 Side Chain Contributions to Human Erythropoietin's Biological Activity by Site–Directed Mutagenesis," *Exp. Hematol.*, 21(8): (Abstract 632) (Aug. 1993).

Boissel, J.P., et al., "Erythropoietin (EPO) Structure–Function Relationships: Identification of Functionally Important Domains," *Blood* 82(10): 316a (Abstract 1250) (Nov. 15, 1993).

Powell, J.S., et al., "Human Erythropoietin Gene: High Level Expression in Stably Transfected Mammalian Cells and Chromosome Localization," *Proc. Natl. Acad. Sci. USA*, 83:6465–6469 (1986).

Tsuda, E., et al., "The Role of Carbohydrate in Recombinant Human Erythropoietin," *Eur. J. Biochem.*, 188:405–411 (1990).

Elder, G.E., et al., "In Vitro Bioassay of Erythropoietic Activity in Serum Using Mouse Spleen Cells. The Effect of Heat Inactivation on Serum Erythropoietin," *Blood Cells*, 11: 409–416 (1986).

Endo, Y., et al., "Heat–Induced Aggregation of Recombinant Erythropoietin in the Intact and Deglycosylated States as Monitored by Gel Permeation Chromatography Combined with a Low–Angle Laser Light Scattering Technique," *J. Biochem.*, 112: 700–706 (1992).

Chern, Y., et al., "Potentiation of the Erythropoietin Response by Dimethyl Sulfoxide Priming of Erythroleukemia Cells: Evidence for Interaction of Two Signaling Pathways," *Blood*, 76(11): 2204–2209 (Dec. 1, 1990).

Yonekura, S., et al., "Erythropoietin Receptors Induced by Dimethyl Sulfoxide Exhibit Positive Cooperatively Associated with an Amplified Biologic Response," *Proc. Natl. Acad. Sci. USA*, 88: 2535–2539 (1991).

McMahon, G.F., et al., "Pharmacokinetics and Effects of Recombinant Human Erythropoietin After Intravenous and Subcutaneous Injections in Healthy Volunteers," *Blood*, 76(9): 1718–1722 (Nov. 1, 1990).

Spivak, J.L. and Hogans, B.B., "The In Vivo Metabolism of Recombinant Human Erythropoietin in the Rat," *Blood*, 73(1): 90–99 (Jan. 1989).

Showers, M., et al., "ALA Replacements Increase the Mitogenic Activity of Human Erythropoietin," *Blood*, 84(10), Suppl. 1: 369a (Abstract 1460) (Nov. 15, 1994).

Shoemaker, C.B., et al. (1986) Mol. Cell. Biol. 6: 849–858.

R103K

R103E

R103N

R103H

R103L

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Val Ser Gly Leu Arg Ser Leu Thr Thr Leu Leu Arg
1               5                   1 0

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Asp Lys Thr Val Ser Gly Leu Arg Ser Leu Thr Thr Leu Leu Arg Ala
1               5                   1 0                  1 5

Leu Gly ( 2 ) INFORMATION FOR SEQ ID NO:3:

( i ) SEQUENCE CHARACTERISTICS:
        ( A ) LENGTH: 58 base pairs
        ( B ) TYPE: nucleic acid
        ( C ) STRANDEDNESS: double (D) TOPOLOGY: linear (ii) MOLECULE TYPE: cDNA (xi) SEQUENCE DESCRIPTION: SEQ ID NO:3:

GGATAAAGCC GTCAGTGGCC TTCGCAGCCT CACCACTCTG CTTCGGGCTC TGGGAGCC 58

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

GGATAAAGCC GTCGCTGGCC TTCGCAGCCT CACGACTCTG CTTCGGG 47

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GCCGTCAGTG CCCTTCGCAG CCTCACGACT CTGCTTCGGG 40

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

GCCGTCAGTG GCGCTCGCAG CCTCACC 27

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

CGTCAGTGGC CTTGCCAGCC TCACGACTCT GCTTCGG 37

(2) INFORMATION FOR SEQ ID NO:8:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
CCCATACCAT AGCGTCAGTG GCCTTGACAG CCTCACGACT CTGCTTCGG                      49
```

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
GGCCTTCGCA GCGCCACGAC TCTGCTTCGG G                                         31
```

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:10:

```
GCCTTCGCAG CCTCGCGACT CTGCTTCGGG C                                         31
```

( 2 ) INFORMATION FOR SEQ ID NO:11:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

```
CGCAGCCTCA CCGCTCTGCT TCGAGCTCTG CGAGCCCTC ACCACTGCGC TTCGAGCTCT           60

GGGAGC                                                                     66
```

( 2 ) INFORMATION FOR SEQ ID NO:12:

( i ) SEQUENCE CHARACTERISTICS:
        ( A ) LENGTH: 59 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:12:

```
GCCTCACCAC TGCGCTTCGA GCTCTGCGAG CCCCTCACCA CTCTGGCTCG GGCTCTGGG           59
```

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:13:

```
CCTCACCACT CTGGCTCGGG CTCTGCG                                              27
```

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:14:

GTGGCCTTCG CGCCCTCACG ACTCTGCTTC 30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

CCTCACCACT GCGCTTCGAG CTCTGGGAGC 30

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:16:

CCTCACCACT CTGGCTCGGG CTCTGGG 27

( 2 ) INFORMATION FOR SEQ ID NO:17:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:17:

CGTCAGTGGC CTTAACAGCC TCACGACTCT GCTTCGG 37

( 2 ) INFORMATION FOR SEQ ID NO:18:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:18:

CGTCAGTGGC CTTGAGAGCC TCACGACTCT GCTTCGG 37

( 2 ) INFORMATION FOR SEQ ID NO:19:

( i ) SEQUENCE CHARACTERISTICS:
        ( A ) LENGTH: 37 base pairs

```
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:19:

CGTCAGTGGC CTTCAGAGCC TCACGACTCT GCTTCGG                                    37

( 2 ) INFORMATION FOR SEQ ID NO:20:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:20:

CGTCAGTGGC CTGCACAGCC TCACGACTCT GCTTCGG                                    37

( 2 ) INFORMATION FOR SEQ ID NO:21:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:21:

CGTCAGTGGC CTTCTCAGCC TCACGACTCT GCTTCGG                                    37

( 2 ) INFORMATION FOR SEQ ID NO:22:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:22:

CGTCAGTGGC CTTAAGAGCC TCACGACTCT GCTTCGG                                    37
```

RECOMBINANT HUMAN ERYTHROPOIETIN MUTANTS AND THERAPEUTIC METHODS EMPLOYING THEM

GOVERNMENT SUPPORT

The invention described herein was supported in whole or in part by Grant No. 38841 from the National Institutes of Health and Grant No. N00014-90-1847 from the U.S. Navy.

RELATED APPLICATIONS

This application is a continuation-in-part application of U.S. Ser. No. 08/113,080, filed Aug. 26, 1993, now abandoned, which is a continuation-in-part application of U.S. Ser. No. 07/920,810, filed Jul. 28, 1992, also now abandoned. The teachings of these related applications are incorporated herein by reference.

BACKGROUND

The glycoprotein hormone erythropoietin regulates the growth and differentiation of red blood cell (erythrocyte) progenitors. The hormone is produced in the fetal liver and adult kidney. Erythropoietin induces proliferation and differentiation of red blood cell progenitors through interaction with receptors on the surface of erythroid precursor cells.

Several approaches have been employed to identify those features of the protein that are relevant to its structure and function. Examination of the homologies among the amino acid sequences of erythropoietin proteins of various species has demonstrated several highly conserved regions (McDonald, J. D., et al., *Mol. Cell. Biol.* 6:842–848 (1986)).

Oligonucleotide-directed mutagenesis has been used to prepare structural mutants of erythropoietin, lacking specific sites for glycosylation. Studies indicate that N-linked carbohydrates are important for proper biosynthesis and/or secretion of erythropoietin. These studies also show that glycosylation is important for in vivo, but not in vitro, biological activity. (Dube, S., et al., *J. Biol. Chem.* 263:17516–17521 (1988); Yamaguchi, K., et al., *J. Biol. Chem.* 266:20434–20439 (1991); Higuchi, M., et al., *J. Biol. Chem.* 267:7703–7709 (1992)).

Studies with monoclonal anti-peptide antibodies have shown that the amino terminus and the carboxy-terminal region (amino acids 152–166) of erythropoietin may be involved with biological activity. It has also been demonstrated that antibodies to amino acids 99–119 and 111–129 block the hormone's biological activity, apparently by binding to two distinct non-overlapping domains (99–110 and 120–129). (Sytkowski, A. J. and Donahue, K. A., *J. Biol. Chem.* 262:1161–1165 (1987)). Thus, it was hypothesized that amino acids 99–129 were important in the formation of a functional region involved in receptor recognition, either through forming a necessary component of the protein's tertiary structure or through direct participation in receptor binding, or both.

Preliminary experiments suggested that alterations in localized secondary structure within the 99–129 region resulted in inactivation of erythropoietin. Therefore, a possible structural role for amino acids 99–129 has been postulated. Recently, a series of experiments indicated that amino acids 99–110 (Domain 1) play a critical role in establishing the biologically active conformation of human erythropoietin. (Chern, Y., et al., *Eur. J. Biochem.* 202:225–229 (1991)).

These Domain 1 mutants, in which a group of three amino acids was deleted and replaced by two different amino acids, were found to be biologically inactive. Furthermore, these mutations in Domain 1 inhibited the secretion of the mutant erythropoietin into cell culture medium. (Chern, Y., et al., *Eur. J. Biochem.* 202:225–229 (1991)). Inhibition of secretion in mammalian cells is consistent with a profound structural change of the polypeptide hormone. Profound structural changes could significantly affect the ability of the hormone to interact with its cognate receptor. Thus, these mutant erythropoietin polypeptides are not suitable for elucidating the structure/function relationship that exists between erythropoietin and its cellular receptor. Nor are these mutants suitable erythropoietin antagonists for use, for example, in therapeutic treatment of polycythemias, or over production of erythropoietin. Thus, it would be beneficial to precisely determine which amino acids are critical to the erythropoietin polypeptide to maintain a stable, biologically active conformation which retains its secretable properties and its ability to bind to the erythropoietin receptor.

Moreover, the precise determination of critical amino acid residues would be useful to alter the biological activity of erythropoietin, either decreasing or increasing one or more biological properties of the protein.

SUMMARY OF THE INVENTION

The present invention relates to isolated DNA encoding mutated erythropoietin proteins which have altered biological activity, yet retain their secretable properties (i.e., secretable erythropoietin proteins). That is, the present invention relates to isolated DNA encoding secretable erythropoietin proteins which have at least one amino acid residue in Domain 1 which differs from the amino acid residue present in the corresponding position of wildtype erythropoietin and which have altered ability to regulate the growth and differentiation of red blood cell progenitors. Domain 1 of the mutants described herein refers to the amino acids which correspond to amino acids 99–110 (SEQ ID NO: 1) of the wildtype recombinant erythropoietin. Altered ability is defined as ability different from that of the wildtype recombinant erythropoietin ability to regulate the growth and differentiation of red blood cell progenitors. As used herein, altered ability to regulate the growth and differentiation of red blood cell progenitor cells refers to biological activity different from wildtype recombinant erythropoietin activity (i.e., altered biological activity relative to wildtype recombinant erythropoietin activity). The mutated erythropoietin proteins of the present invention can be secreted in homologous and heterologous expression systems. For example, the mutated erythropoietin proteins of the present invention can be secreted in mammalian, bacterial or yeast expression systems.

The present invention also relates to the modified secretable mutant erythropoietin proteins encoded by the isolated DNA described above. These modified secretable erythropoietin proteins have altered biological activities. For example, the modified secretable mutant erythropoietin may have decreased ability relative to wildtype erythropoietin protein to regulate growth and differentiation of red blood cell progenitor cells. As used herein, decreased ability to regulate growth and differentiation of red blood cell progenitor cells is also referred to as decreased biological activity relative to wildtype erythropoietin activity. Wildtype erythropoietin activity is also referred to herein as biological activity of wildtype erythropoietin. Alternately, a modified secretable mutant erythropoietin protein described herein may exhibit increased heat stability relative to wildtype erythropoietin protein.

The modified erythropoietin proteins described herein comprise an amino acid sequence with at least one amino acid residue different from the amino acid residue present at the corresponding position in Domain 1 in the wildtype erythropoietin. These erythropoietin proteins are referred to as modified secretable human recombinant erythropoietin proteins having altered ability (i.e., decreasing or enhancing ability) relative to wildtype erythropoietin protein to regulate the growth and differentiation of red blood cell progenitors.

The term modified, as used herein, includes substitution of a different amino acid residue, or residues, as well as deletion or addition of an amino acid residue, or residues.

Until the present invention, mutations within the erythropoietin sequence which result in the alteration of biological activity have also frequently resulted in a concurrent loss of secretability of the protein from transfected cells. This loss of secretability is consistent with a loss of structural integrity. (Boissel, J-P. and Bunn, H. F., "The Biology of Hematopoiesis", pp. 227–232, John Wiley and Sons, New York (1990)). Now, the sites critical to the maintenance of a stable, biologically active conformation have been identified by means of oligonucleotide-directed mutagenesis and have been found to occur in Domain 1 (amino acids 99–110) (SEQ ID NO: 1) of human recombinant erythropoietin. Modifications of the wildtype erythropoietin have been made and the encoded erythropoietin proteins have been expressed. The resulting mutant erythropoietin proteins described herein have altered erythropoietin regulating activity, as demonstrated in the art-recognized bioassay of Krystal, G., *Exp. Hematol.* 11:649–660 (1983). Activity of the resulting erythropoietin proteins has also been evaluated by commercially available radioimmunoassay protocols.

In particular, the arginine 103 site is essential for erythropoietin activity. As shown herein, replacement of the arginine 103 by another amino acid results in a modified erythropoietin with significantly decreased biological activity relative to wildtype erythropoietin activity. Modifications at this site, as well as other sites within Domain 1, can similarly be made to enhance regulating activity, as well as to decrease, or reduce regulating ability.

The modified secretable erythropoietin proteins described herein provide useful reagents to further elucidate the structure/function relationship of erythropoietin and its cellular receptor.

Such modified secretable erythropoietin proteins with altered regulating ability can also be used for therapeutic purposes. For example, modified erythropoietin proteins with enhanced biological activity would be a more potent therapeutic, therefore requiring a lower effective dose or less frequent administration to an individual. Erythropoietin proteins with decreased biological activity that still retain their structural integrity and bind to their cognate receptor would be useful to decrease growth and differentiation of red blood cell precursors in certain leukemias and polycythemias. Furthermore, an erythropoietin protein that selectively triggers only certain events within the red blood cell precursor cell would be useful in treating various hematological conditions.

Further, it is expected that modified secretable mutant erythropoietin proteins with increased heat stability relative to wildtype erythropoietin proteins would have a longer plasma half-life relative to wildtype erythropoietin proteins. Thus, such modified erythropoietin proteins with increased heat stability can be useful therapeutically. For example, modified secretable mutant erythropoietin proteins with increased heat stability would be especially important in patients with a fever and/or experiencing an increased metabolic state.

The present invention also relates to methods of modifying or altering the regulating activity of a secretable erythropoietin protein.

This invention further relates to pharmaceutical compositions comprising an effective amount of modified secretable human recombinant erythropoietin in a physiologically acceptable carrier.

The present invention also relates to a method of evaluating a substance for ability to regulate growth and differentiation of red blood cell progenitor cells.

BRIEF DESCRIPTION OF THE DRAWINGS

FIG. 6A shows the activity of R103A. FIG. 6B shows the activity of R103D. FIG. 6C shows the activity of R103K. FIG. 6D shows the activity of R103E. FIG. 6E shows the activity of R103N. FIG. 6F shows the activity of R103Q. FIG. 6G shows the activity of R103H. FIG. 6H shows the activity of R103L.

DETAILED DESCRIPTION OF THE INVENTION

Figure 1:
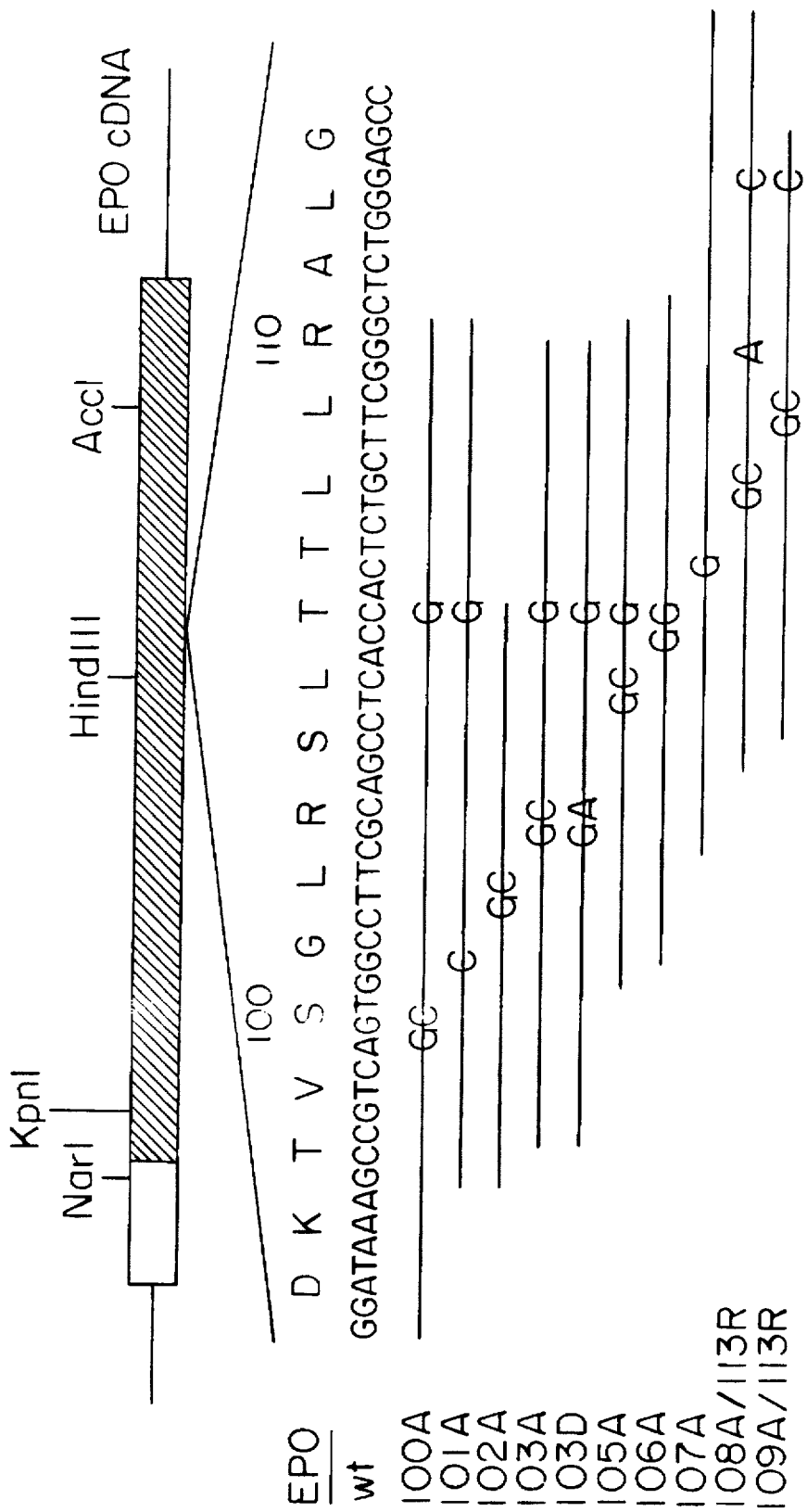
FIG. 1 is a schematic diagram of the in vitro mutagenesis protocol. WT=wildtype erythropoietin. Shown are SEQ ID NOS: 2/3 respectively.

The present invention is based on the identification of amino acid residues of the erythropoietin polypeptide which are critical for its biological activity and secretable properties. These sites have been precisely defined through oligonucleotide-directed mutagenesis and used to create mutant human recombinant erythropoietin proteins which are altered by one, or more, amino acid substitutions and thus differ from wildtype erythropoietin.

Identification of Amino Acid Residues of Human Recombinant Erythropoietin Critical for Biological Activity Previously, anti-peptide antibodies to several hydrophilic domains of the erythropoietin molecule had demonstrated that antibodies to amino acids 99–110 (Domain 1) and 111–129 (Domain 2) block the hormone's biological activity. Binding of the antibody to a portion of the erythropoietin molecule that participated in receptor recognition would block such recognition, thereby neutralizing erythropoietin's biological activity. (Sytkowski, A. J. and Donahue, K. A., *J. Biol. Chem.* 262:1161–1165 (1987)).

A series of mutants across the 99–129 region was produced by sequentially replacing three amino acids with Glu-Phe. Mutations in amino acid residues 99–110 caused a profound structural change which inhibited secretion of the mutant erythropoietin after biosynthesis. (Chern, Y., et al., *Eur. J. Biochem.* 202:225–229 (1991)). To precisely identify the amino acid site, or sites, critical for receptor recognition and biological activity, amino acids 100–109 were studied by alanine scanning mutagenesis, as described in detail in Example 1.

Briefly, human recombinant erythropoietin cDNA (Powell, J. W., et al., *Proc. Natl. Acad. Sci. USA* 83:6465–6469 (1986)) was inserted into the Phagemid vector pSELECT (Promega Corp., Madison, Wis.) which contains two genes for antibiotic resistance. One of these genes, specific for tetracycline resistance is always functional, while the other, specific for ampicillin resistance, has been inactivated. The single-stranded template for the mutagenesis reaction was prepared by growing cultures of bacteria transformed with the Phagemid and infected with a helper phage. The resulting single-stranded DNA was isolated.

Two oligonucleotides were annealed to this recombinant ssDNA template. The first oligonucleotide was an ampicillin repair oligo designed to convert the vector to ampicillin resistance and the second oligonucleotide was a mutagenic oligo designed to change a portion of the erythropoietin cDNA sequence.

Subsequently, the mutant second strand was synthesized in vitro using T4 DNA polymerase and ligated. This DNA was then transformed into a repair minus strain of *E. coli* and these cells were grown in the presence of ampicillin. The phagemid was then harvested and a second round of transformation was carried out and mutants were selected on ampicillin plates. This resulted in the production of a double stranded phagemid containing both the ampicillin resistance gene and the mutated erythropoietin cDNA.

FIG. 1 shows the region of the erythropoietin cDNA encoding amino acids 96–113 (SEQ ID NO: 2) and the corresponding wildtype erythropoietin DNA sequence encoding amino acids 96–113 (SEQ ID NO: 3). The column of numbers on the left hand side of FIG. 1 indicates the amino acid substitution. The only amino acid residue substitutions made were as indicated. The remainder of the human recombinant erythropoietin DNA sequence was not altered. (The remaining, unaltered human recombinant DNA sequence is not shown.) Thus, for example, 100A (SEQ ID NO: 4) indicates that amino acid 100, normally a serine residue, was replaced by alanine, 101A (SEQ ID NO: 5) indicates that glycine 101 was replaced by alanine, and so forth (SEQ ID NOS: 6–16).

Some sites were mutated more than once. For example, amino acid 103 was mutated twice. The first mutation was the substitution of alanine for arginine 103 (SEQ ID NO: 7) and the second substitution was aspartic acid for arginine (SEQ ID NO: 8).

Two double mutants were also produced, 108A/113R (SEQ ID NO: 12) and 109A/113R (SEQ ID NO: 13). In these two instances, amino acids 108 and 109 were each substituted with alanine in the second mutation and the replacement of glycine 113 with arginine was introduced. The changes in nucleotide sequence in each mutagenic oligo are indicated in FIG. 1 and Table I (SEQ ID NOS: 4–22). In Table I, the underlined nucleotides are those which differ from the wildtype erythropoietin sequence. A silent mutation designed to introduce a restriction site, Hinf I, allowing convenient initial screening for mutated erythropoietin cDNAs, was also introduced.

In addition, two mutants in the region of the erythropoietin cDNA encoding amino acids 1–26 (the aminoterminus region) were produced. In these two instances, amino acid 14, normally an arginine, was replaced either by alanine (14A) or aspartic acid (14D).

Figure 2:
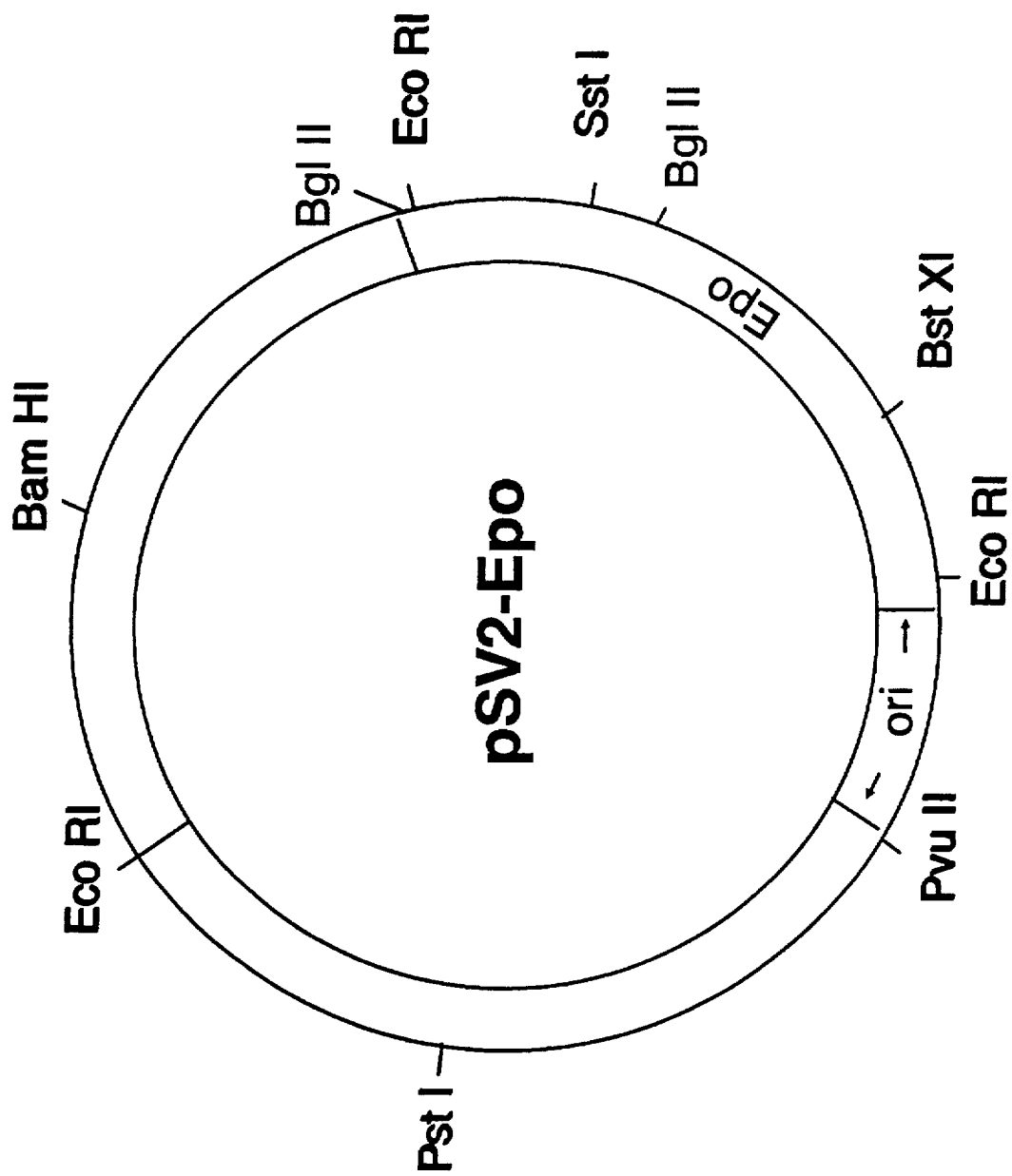
FIG. 2 depicts the structure of expression vector pSV-2-erythropoietin.

Each mutated erythropoietin cDNA was identified by restriction analysis, using standard laboratory protocols, and its structure was confirmed by DNA sequencing. The mutated erythropoietin cDNA was then inserted into the expression vector pSV-2 (FIG. 2) using standard laboratory techniques. (Mulligan, R. C., et. al. *Nature* 277:108–114 (1979); Maniatis, T., et al., "Molecular Cloning: A Laboratory Manual", Cold Spring Harbor Laboratories, New York (1982)).

As described in detail in Example 2, COS-7 cells were transfected with the pSV-2-erythropoietin constructs. After three days, the supernatant medium was harvested and the biological activity of the mutant erythropoietin proteins and wildtype erythropoietin was measured by the Krystal bioassay (Krystal, G., *Exp. Hematol.* 11:649–660 (1983)). Briefly, the bioassay of Krystal measures the effect of erythropoietin on intact mouse spleen cells. Mice were treated with phenylhydrazine to stimulate production of erythropoietin-responsive red blood cell progenitor cells. After treatment, the spleens were removed, intact spleen cells were carefully isolated and incubated with various amounts of wildtype erythropoietin or the mutant erythropoietin proteins described herein. After an overnight incubation, $^3$H thymidine was added and its incorporation into cellular DNA was measured. The amount of $^3$H thymidine incorporation is indicative of erythropoietin-stimulated production of red blood cells via interaction of erythropoietin with its cellular receptor. The concentration of mutant erythropoietin protein, as well as the concentration of wildtype erythropoietin, was quantified by competitive radioimmunoassay (Incstar, Stillwater, Minn.). Specific activities were calculated as international units measured in the Krystal bioassay divided by micrograms as measured as immunoprecipitable protein by RIA. Both assays used wildtype recombinant human erythropoietin standardized against the World Health Organization Second International Reference Standard preparation.

Figure 3:
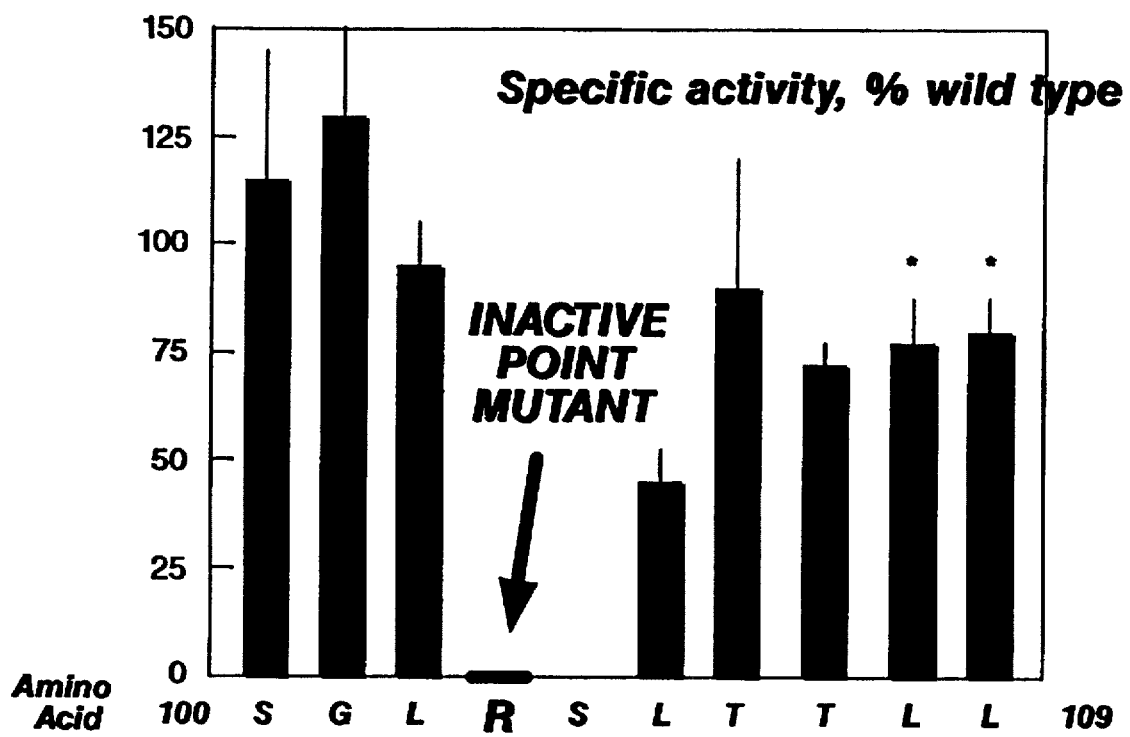
FIG. 3 is a graphic representation of the specific activities of nine mutant erythropoietin proteins.
Figure 4:
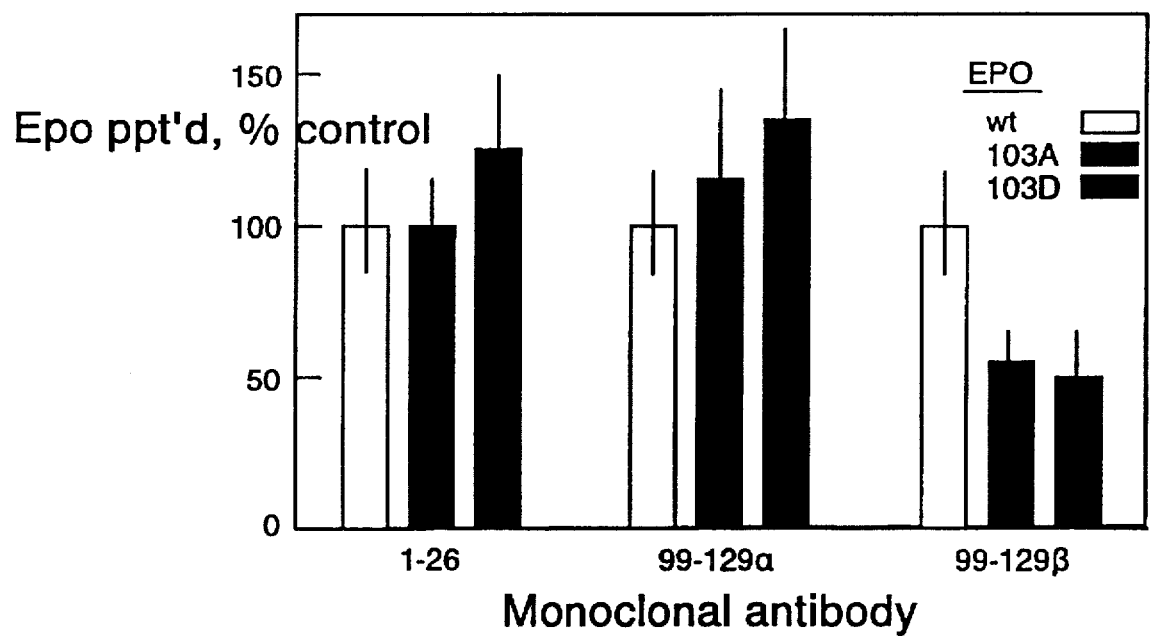
FIG. 4 is a graphic representation of the results of monoclonal antibody precipitation of the mutant erythropoiein proteins.
Figure 5:
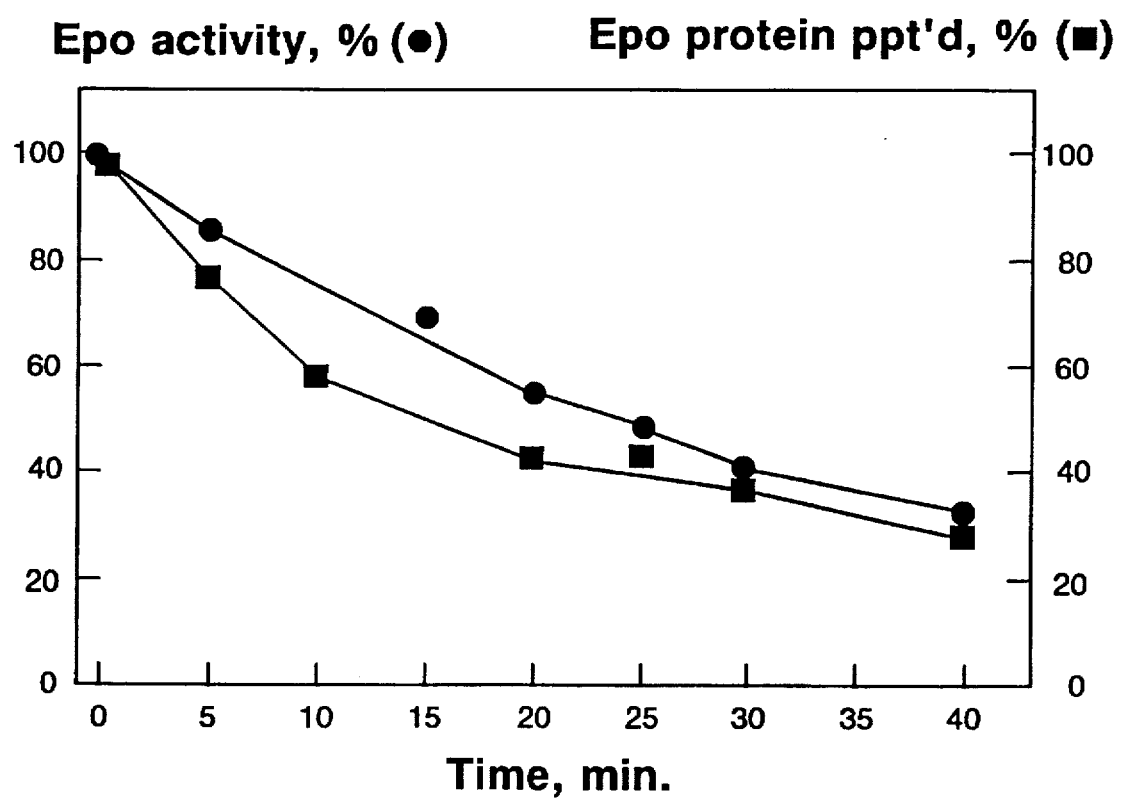
FIG. 5 is a graphic representation of the activity of heat-denatured wildtype erythropoietin as measured by radioimmunoassay (■) and the Krystal bioassay (●).

Two sets of experiments were performed in order to determine the specific biological activities of these mutant erythropoietin proteins. Specific activities of nine of the mutant erythropoietin proteins (SEQ ID NOS: 4–13) assayed in the first set of experiments are shown in FIG. 3. As shown in FIG. 3, the specific activities are presented as a percent of the wildtype erythropoietin activity for each mutant erythropoietin. The amino acid replaced by alanine is indicated along the horizontal axis. Table I also shows the specific activities of the nine mutant erythropoietin proteins (SEQ ID NOS: 4–13) as well as nine additional mutant erythropoietin proteins (SEQ ID NOS: 14–22) again assayed in the first set of experiments. The specific activity noted in Table I is also that activity relative to wildtype erythropoietin's activity, which is set at 100%.

As shown in Table I, substitution of alanine for serine 104 decreased activity to approximately 16% of wildtype erythropoietin (SEQ ID NO: 14). Substitution of alanine for leucine 105 (SEQ ID NO: 9) reduced the activity to approximately 44 percent of wildtype erythropoietin. Substitution of alanine for leucine 108 (SEQ ID NO: 15) reduced the activity to approximately 37% of wildtype erythropoietin.

TABLE I

ALANINE SCANNING MUTAGENESIS OF AMINO ACIDS
100–109 OF ERYTHROPOIETIN

| MUTANT | OLIGONUCLEOTIDE | SPECIFIC ACTIVITY | SEQ ID NO: |
|---|---|---|---|
| S100A | GGATAAAGCCGTCGCTGGCCTTCGCAGCCTCACGACTCTGCTTCGGG | 107.9% | 4 |
| G101A | GCCGTCAGTGCCCTTCGCAGCCTCACGACTCTGCTTCGGG | 126.8% | 5 |
| L102A | GCCGTCAGTGGCGCTCGCAGCCTCACC | 93.3% | 6 |
| R103A | CGTCAGTGGCCTTGCCAGCCTCACGACTCTGCTTCGG | 0.0% | 7 |
| R103D | CGTCAGTGGCCTTGACAGCCTCACGACTCTGCTTCGG | 0.0% | 8 |
| L105A | GGCCTTCGCAGCGCCACGACTCTGCTTCGGG | 44.0% | 9 |
| T106A | GCCTTCGCAGCCTCGCGACTCTGCTTCGGGC | 76.9% | 10 |
| T107A | CGCAGCCTCACCGCTCTGCTTCGAGCTCTGCGAGCC | 86.6% | 11 |
| L108A/G113R | GCCTCACCACTGCCTTCGAGCTCTGCGAGCC | 77.3% | 12 |
| L109A/G113R | CCTCACCACTCTGGCTCGGGCTCTGCG | 84.7% | 13 |
| S104A | GTGGCCTTCGCGCCCTCACGACTCTGCTTC | 16.3% | 14 |
| L108A | CCTCACCACTGCGCTTCGAGCTCTGGGAGC | 36.9% | 15 |
| L109A | CCTCACCACTCTGGCTCGGGCTCTGGG | 70.2% | 16 |
| R103N | CGTCAGTGGCCTTAACAGCCTCACGACTCTGCTTCGG | 0.0% | 17 |
| R103E | CGTCAGTGGCCTTGAGAGCCTCACGACTCTGCTTCGG | 0.0% | 18 |
| R103Q | CGTCAGTGGCCTTCAGAGCCTCACGACTCTGCTTCGG | 0.0% | 19 |
| R103H | CGTCAGTGGCCTTCACAGCCTCACGACTCTGCTTCGG | 0.0% | 20 |
| R103L | CGTCAGTGGCCTTCTCAGCCTCACGACTCTGCTTCGG | 0.0% | 21 |
| R103K | CGTCAGTGGCCTGAAGAGCCTCACGACTCTGCTTCGG | 10.2% | 22 |

To further characterize the muteins obtained by substitution of the 103 arginine amino acid residue (SEQ ID NOS: 7, 8 and 17–22), a second set of experiments with COS-7 cells transfected as described in Example 2 with the pSV-2-erythropoietin mutant constructs encoding these muteins was performed. The supernatant medium was again harvested after three days and the biological activity of the mutant erythropoietin proteins was measured by the Krystal bioassay, the concentration of mutant erythropoietin protein was quantified by competitive radioimmunoassay (Incstar, Stillwater, Minn.) and specific activities (shown in Table II) were calculated as international units measured in the Krystal bioassay divided by micrograms as measured as immunoprecipitable protein by RIA.

The results show that these three mutant erythropoietin proteins (SEQ ID NOS: 20–22) have some intrinsic agonist activity (biological activity), thus indicating that the erythropoietin muteins (SEQ ID NOS: 20–22) must bind to the erythropoietin receptor. This phenomenon of weak agonist activity is commonly seen in pharmacologic blockers when tested at high enough concentrations. Thus, it is reasonable to predict that equivalent quantities of these extremely low activity muteins would compete effectively with native erythropoietin and block activity.

As shown in Table II, mutants having arginine 103 substituted by alanine (SEQ ID NO: 7), aspartic acid (SEQ ID NO: 8), asparagine (SEQ ID NO: 17), glutamic acid (SEQ ID NO: 18), and glutamine (SEQ ID NO: 19) exhib-

TABLE II

MUTAGENESIS OF AMINO ACID
Arg 103 OF ERYTHROPOIETIN

| MUTANT | OLIGONUCLEOTIDE | SPECIFIC ACTIVITY | SEQ ID NO: |
|---|---|---|---|
| R103A | CGTCAGTGGCCTTGCCAGCCTCACGACTCTGCTTCGG | 0.0% | 7 |
| R103D | CGTCAGTGGCCTTGACAGCCTCACGACTCTGCTTCGG | 0.0% | 8 |
| R103N | CGTCAGTGGCCTTAACAGCCTCACGACTCTGCTTCGG | 0.0% | 17 |
| R103E | CGTCAGTGGCCTTGAGAGCCTCACGACTCTGCTTCGG | 0.0% | 18 |
| R103Q | CGTCAGTGGCCTTCAGAGCCTCACGACTCTGCTTCGG | 0.0% | 19 |
| R103H | CGTCAGTGGCCTTCACAGCCTCACGACTCTGCTTCGG | 1.7% | 20 |
| R103L | CGTCAGTGGCCTTCTCAGCCTCACGACTCTGCTTCGG | 0.4% | 21 |
| R103K | CGTCAGTGGCCTGAAGAGCCTCACGACTCTGCTTCGG | 25.0% | 22 |

As shown in Table II, mutants having arginine 103 substituted by histidine (SEQ ID NO: 20) exhibited decreased activity to approximately 1.7% of wildtype erythropoietin. Specific activity is again defined as percent activity of wildtype erythropoietin activity. Mutants having arginine 103 substituted by leucine (SEQ ID NO: 21) exhibited decreased activity to approximately 0.4% of wildtype erythropoietin. Mutants having arginine 103 substituted by lysine (SEQ ID NO: 22) exhibited decreased activity to approximately 25% of wildtype erythropoietin compared to approximately 10% of wildtype erythropoietin shown previously (compare Table I and Table II).

ited essentially no erythropoietin biological activity as was shown previously (Table I). The results of these experiments indicate that amino acid position 103 is important for erythropoietin biological activity. Although all of these mutants were expressed and secreted into culture medium at rates equivalent to that seen for wildtype and other mutants, only very low levels of biological activity were detected or, in some cases, no biological activity was detected. Methods described herein, such as the ex vivo bioassay of Krystal (Krystal, G., Exp. Hematol. 11:649–660 (1983)), which is an art-recognized bioassay used to evaluate erythropoietin activity, showed that these inactive arginine 103 mutants are reduced in activity by at least a 1000-fold below that of the wildtype human recombinant erythropoietin.

Figure 6A:
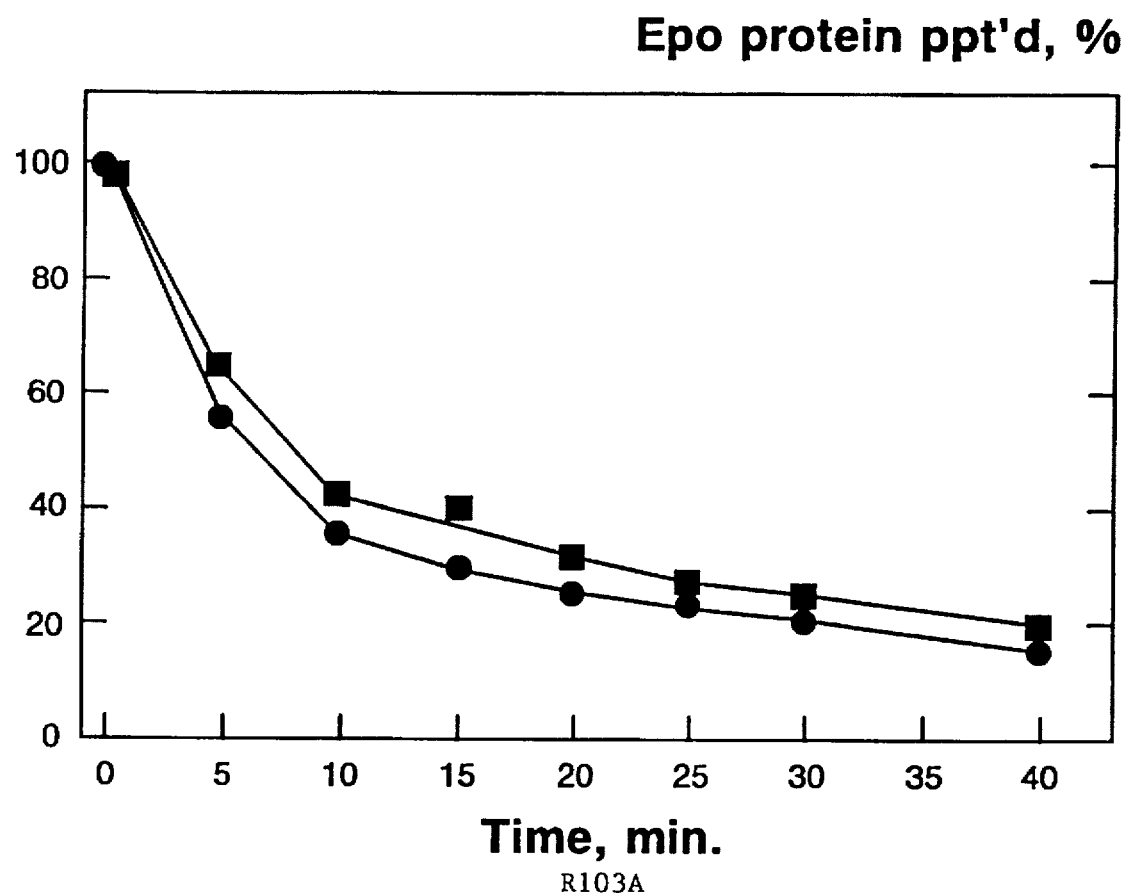
FIGS. 6A–6H are graphic representations of the activity of the 103 mutant erythropoietin proteins as measured by radioimmunoassay (■) and the activity of wildtype erythropoietin (●).
Figure 6B:
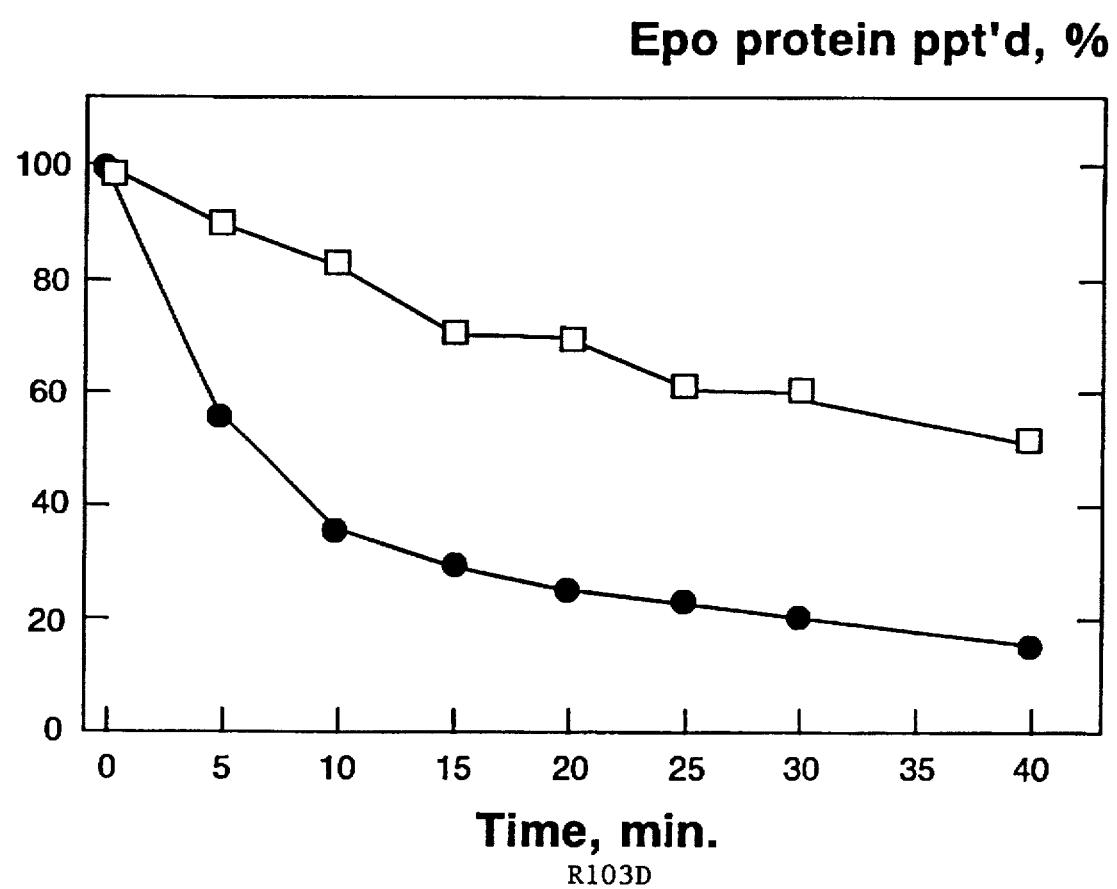
Figure 6C:
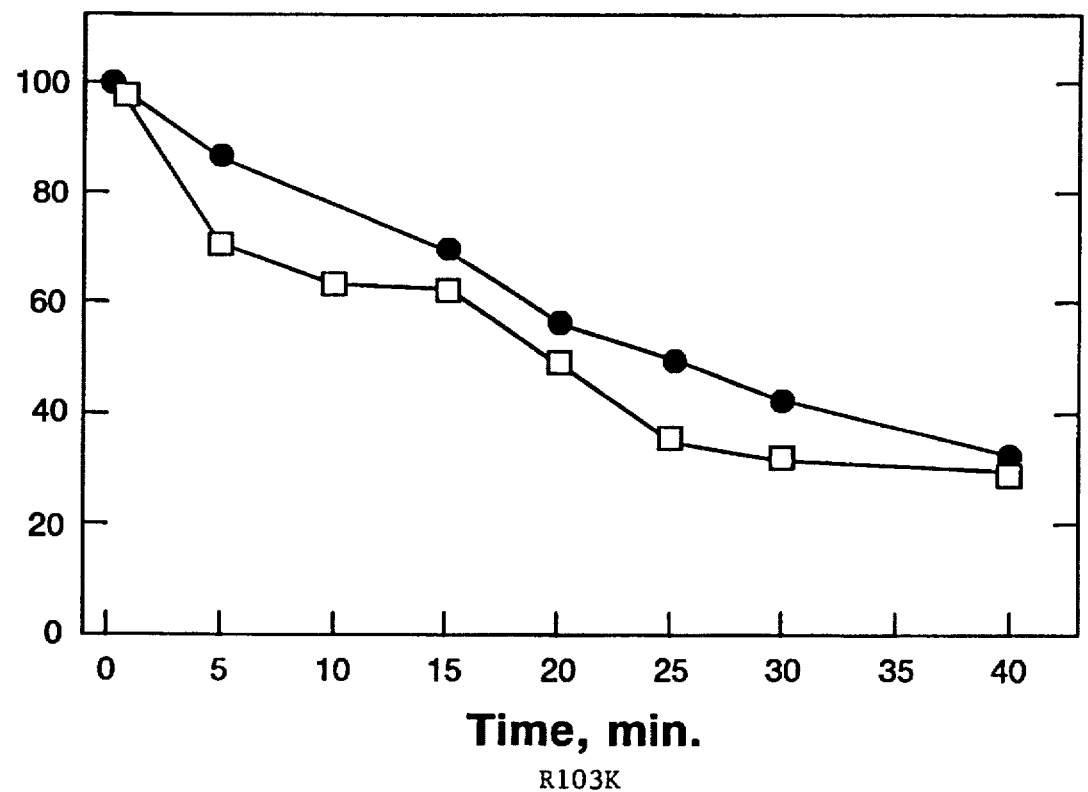
Figure 6D:
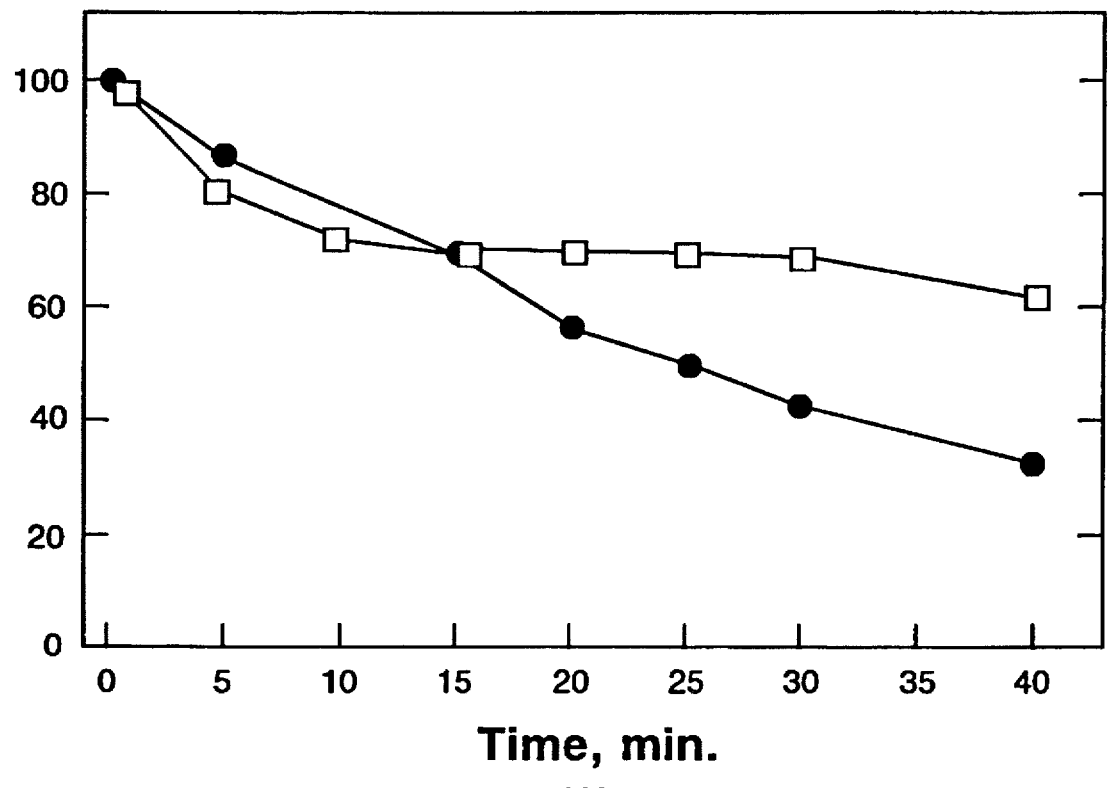
Figure 6E:
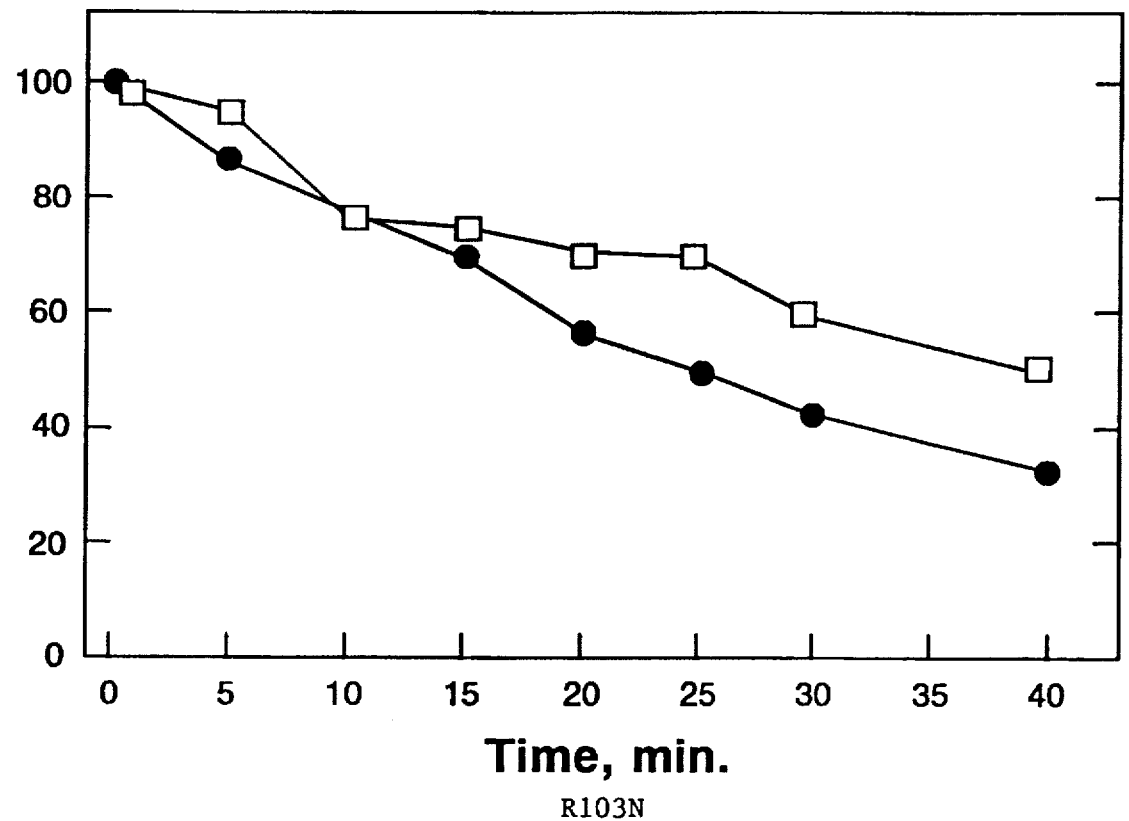
Figure 6F:
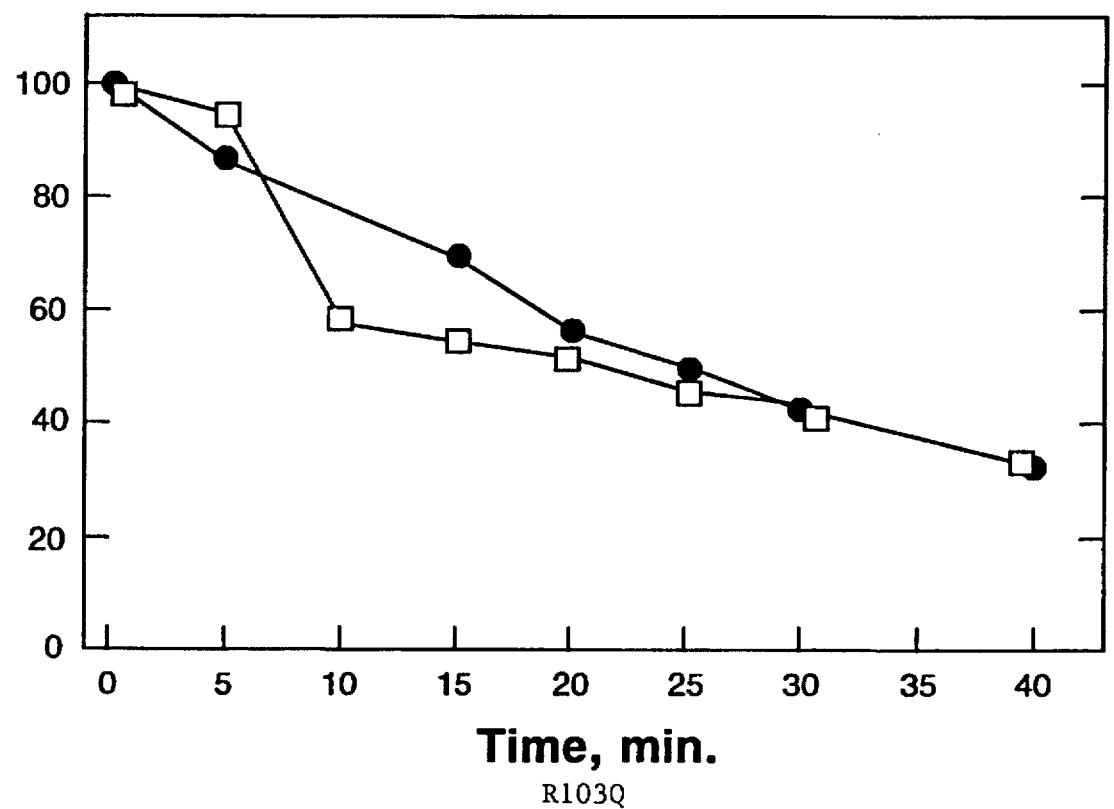
Figure 6G:
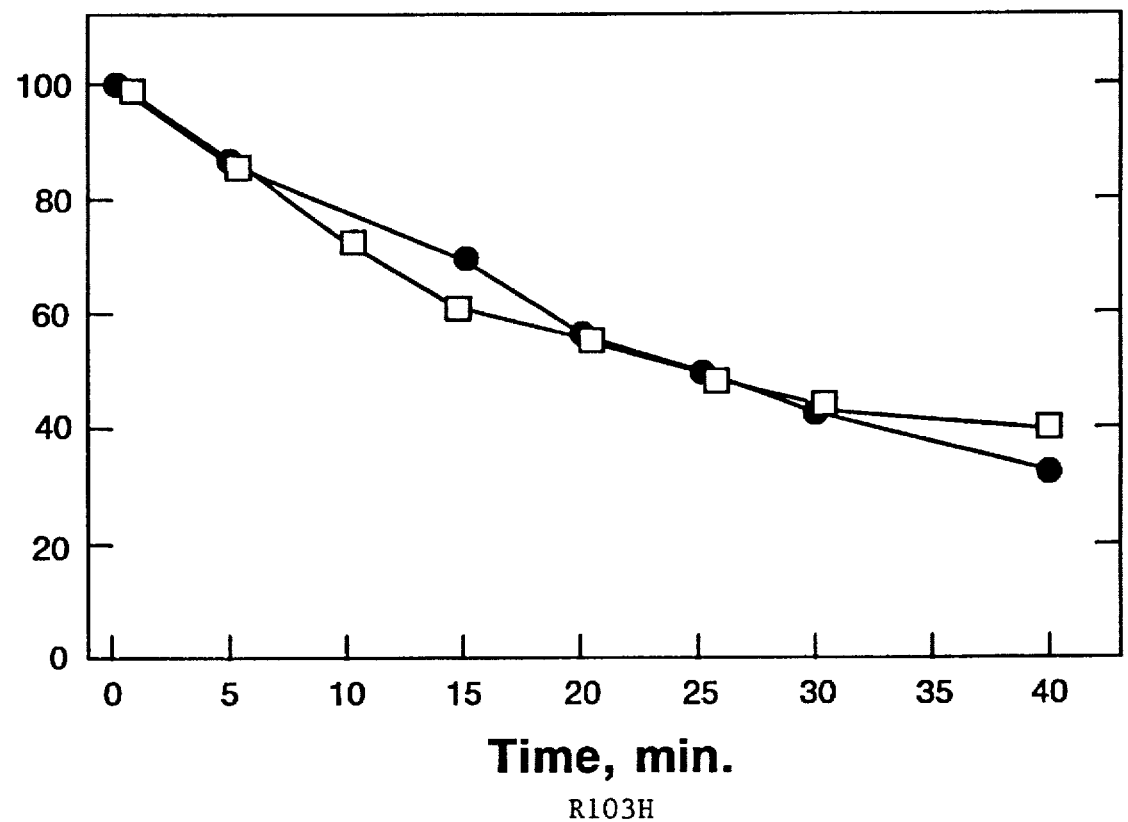
Figure 6H:
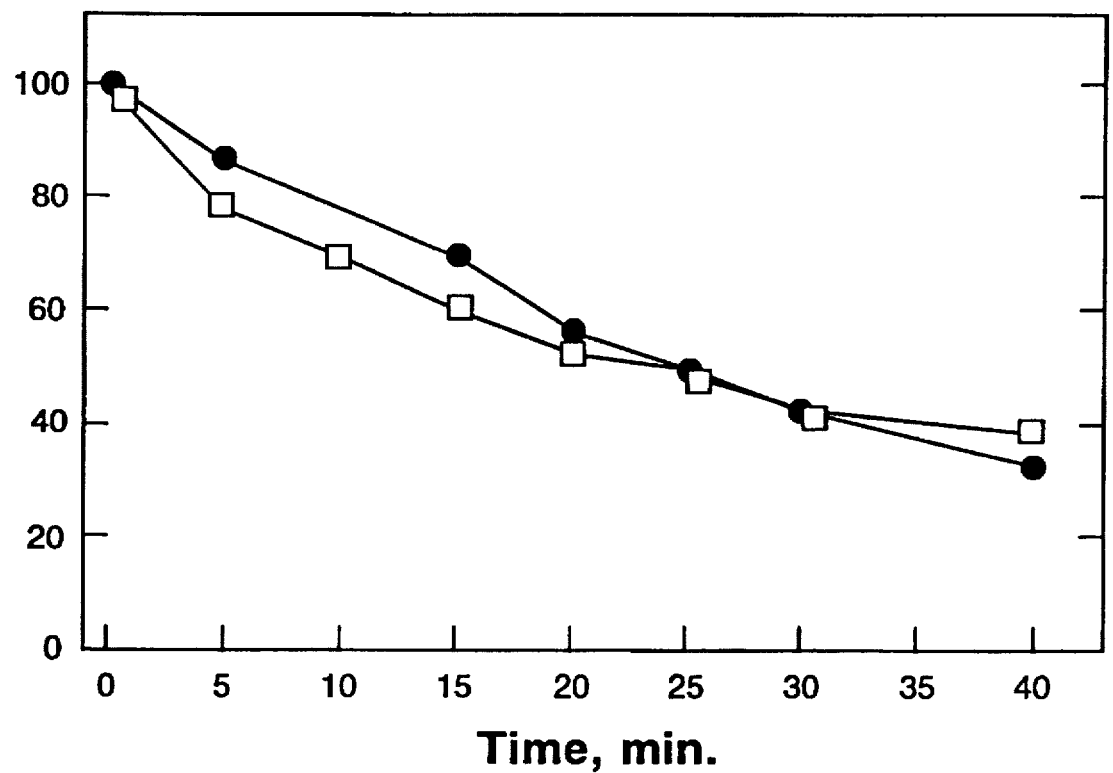

Previously published studies indicated that mutations in the Domain 1 region resulted in biologically inactive muteins. (Chern, Y., et al., *Eur. J. Biochem.* 202:225–229 (1991)). Thus, modified secretable erythropoietin proteins with mutations in the Domain 1 region would not be expected to have enhanced biological activity relative to wildtype erythropoietin proteins. That is, making mutations in this critical and highly conserved region of the erythropoietin protein would not be expected to result in the production of muteins with increased specific activity relative to wildtype erythropoietin proteins. Surprisingly, as shown in Table I, substitution of alanine for serine 100 (SEQ ID NO: 4) and glycine 101 (SEQ ID NO: 5) increased the specific activity of these mutant proteins.

To determine if the increased specific activity of the muteins obtained by substitution of alanine for serine 100 (S100A; SEQ ID NO: 4) and glycine 101 (G101A; SEQ ID NO: 5) was statistically significant, a statistical analysis based on the Student-t distribution for small samples was performed. The mean values obtained were compared to that of wildtype erythropoietin activity using the "difference between two sample means" statistic (one-sided). The increased specific activity of G101A over wildtype was found to be statistically significant at the 0.05 level of significance. The increased specific activity of S100A was not found to be statistically significant below the 0.010 level of significance.

Additionally, mutants having arginine 14 substituted by alanine (R14A) exhibited decreased activity to approximately 16.4 % of wildtype erythropoietin. Mutants having arginine 14 substituted by aspartic acid (R14D) exhibited decreased activity to approximately 3.9% of wildtype erythropoietin.

Structural Integrity of Mutant Erythropoietin Proteins

Previously published studies indicated that mutations in the Domain 1 region in which a group of three amino acids was deleted and replaced with Glu-Phe, caused pronounced structural changes in the molecule. (Chern, Y., et al., *Eur. J. Biochem.* 202:225–229 (1991)). These structural changes were accompanied by lack of secretion of the mutant erythropoietin from the transfected COS-7 cells. Surprisingly, this phenomenon was not observed with the more subtle mutations of the present invention. Thus, the mutant erythropoietin proteins described herein provide structurally intact (i.e., with the proper biological conformation) mutant erythropoietin proteins.

Assessment of the structural integrity of the mutated erythropoietin proteins of the instant invention was performed by a series of immunoprecipitation experiments using anti-peptide monoclonal antibodies to two domains of the protein, as described in Example 3.

Briefly, the first monoclonal antibody recognizes an epitope within amino acids 1–26 of erythropoietin. The other monoclonal antibodies recognize distinct epitopes within amino acids 99–129. It is known that a gross change in the tertiary structure of erythropoietin would result in an inability of one or more of the monoclonal antibodies to recognize the erythropoietin molecule. For example, it has been demonstrated that radio-iodination of erythropoietin in the presence of chloramine-T denatures the molecule, resulting in loss of biological activity and corresponding loss of recognition by monoclonal antibody.

FIG. 4 shows mutant erythropoietin protein precipitated as percent of control of wildtype erythropoietin precipitated using three monoclonal antibodies designated across the horizontal axis, 1–26, 99–129α and 99–129β. The three erythropoietin proteins examined were the wildtype erythropoietin, the 103 alanine mutant and the 103 aspartic acid mutant. As seen on the left side of the graph, monoclonal 1–26 recognized each of the three recombinant erythropoietin proteins with equal efficiency, indicating that mutation of amino acid 103 to either alanine or aspartic acid did not result in a gross distortion of erythropoietin's conformation.

Similarly, as shown in the center of the graph, monoclonal 99–129β also recognized the wildtype 103 alanine mutant and 103 aspartic acid mutant with no statistically significant difference among them. This indicates that the conformation within the amino acids 99–129 is similar among the three recombinant erythropoietin proteins.

Lastly, as shown on the right side of the graph, monoclonal 99–12962 recognized both mutant erythropoietin proteins with approximately half the efficiency as it recognized the wildtype erythropoietin. This is consistent with the subtle structural change introduced by a single amino acid mutation. Taken together, it is reasonable to assume that the inactive point mutants, 103 alanine and 103 aspartic acid, are not grossly denatured.

Heat Stability of Mutant Erythropoietin Proteins

A previously published study indicated that recombinant human erythropoietin aggregates as temperature rises. (Endo, Y., et al., *J. Biochem.* 112(5):700–706 (1992)). Most of the erythropoietin molecules within these multimeric aggregates (twenty erythropoietin molecules per aggregate) would almost certainly not be detectable by antibodies in a radioimmunoassay (RIA). Surprisingly, heat reduced the RIA detection of wildtype erythropoietin much more rapidly than the more stable mutants of the present invention. Thus, some of the mutant erythropoietin proteins described herein demonstrate increased heat stability relative to the wildtype erythropoietin protein.

Assessment of the heat stability of the mutated erythropoietin proteins of the instant invention was performed by comparing in vitro biological activity with antibody reactivity. Briefly, aliquots of conditioned medium from erythropoietin cDNA-transfected COS cells were incubated at 56° C. for specified time intervals. The samples were cooled on ice and a fraction of each was assessed for biological activity in the Krystal bioassay. The remainder was split into two fractions and erythropoietin protein was quantified by radioimmunoassay using the commercially available INCSTAR RIA kit. The results are given in terms of the percent biological activity remaining or percent protein immunoprecipitated after heat treatment compared to untreated samples.

Wildtype erythropoietin exhibits a time-dependent decrease in biological activity when incubated at 56° C. or above (FIG. 5); Tsuda, E., et al., *Eur. J. Biochem.* 188:405–411 (1990). Interestingly, a corresponding decrease in the ability of the commercial radioimmunoassay's antibodies to recognize this heat-denatured erythropoietin was also observed (FIG. 5). This observation was quite reproducible and enabled the use of the RIA to measure the heat stability of the inactive R103A erythropoietin compared to that of wildtype erythropoietin. As seen in FIG. 6A, the heat denaturation curves of R103A and wildtype erythropoietin are essentially identical.

To confirm that this heat stability comparison is sensitive to mutations in this region of erythropoietin, the effect of the aspartic acid substitution (R103D) on the protein's stability was evaluated. The introduction of a negatively charged amino acid residue would reasonably be more structurally disruptive to the molecule than an alanine, and thus be more likely to alter the protein's heat-denaturation curve. The heat stability of R103D was markedly different (i.e., greater) than that of wildtype erythropoietin and R103A, as anticipated (FIG. 6B).

To further characterize the nature of the interaction between amino acid residue 103 and the erythropoietin receptor, site-directed mutagenesis was used to produce erythropoietin analogs with altered side chain properties at this position. Arginine was substituted with histidine (R103H), lysine (R103K), asparagine (R103N), glutamine (R103Q), leucine (R103L) and glutamic acid (R103E) to generate 6 new altered erythropoietin molecules. Culture supernatants of cells transfected with these constructs in a first set of experiments were tested in the Krystal bioassay and the heat stability assay for biological activity and structural stability, respectively.

The heat denaturation curve of R103K was essentially identical to that generated for the wildtype protein. Interestingly, the heat denaturation curve for R103E was notably different from that of wildtype, and very similar to that of R103D. The other 4 mutants had denaturation kinetics intermediate to that of these two proteins. (See FIGS. 6C–6H).

Production of Additional Erythropoietin Proteins Having Altered Biological Activity As a result of the identification of sites which are critical to erythropoietin activity in terms of the amino acid residue present and which can be altered to produce a mutated sequence which has altered biological activity but retains its structural integrity, it is now possible to produce modified secretable human recombinant erythropoietin proteins whose ability to regulate the growth and differentiation of red blood cell progenitors is altered (i.e., whose ability to regulate red blood cell progenitors is different from that of the corresponding wildtype human recombinant erythropoietin). These modified human recombinant erythropoietin proteins can be secreted in homologous or heterologous expression systems.

As described in the previous sections and in the Examples, such sites have been identified by oligonucleotide-directed mutagenesis and used to create mutant erythropoietin which resulted in substitution of amino acids at positions 100–109 within Domain 1 (SEQ ID NO: 1), as represented in FIG. 1 (SEQ ID NOS: 4–13) and Table I (SEQ ID NOS: 4–16). The data indicate that arginine 103 is critical for erythropoietin's biological activity. Additionally, serine 104, leucine 105 and leucine 108 appear to play a role, as indicated by the decreased biological activity of these mutants as measured in the above-described bioassays.

It is important to note that the ability of erythropoietin to regulate growth and differentiation of red blood cell progenitors depends on the ability of erythropoietin to bind to its cellular receptor. Importantly, the mutations described herein do not disrupt the structural integrity of the erythropoietin protein, as evidenced by the fact that the mutated protein is secreted. That is, as the data presented herein indicate, these mutant erythropoietin proteins retain their biological conformation. These results also indicate that Domain 1 amino acids 99–110 very likely participate in receptor recognition and activation.

Moreover, as the data presented herein indicate, some mutant erythropoietin proteins also demonstrate increased heat stability relative to the wildtype erythropoietin, even though the biological activity of the mutant has been significantly decreased.

Substitution of alanine at arginine 103 produced erythropoietin mutants with no detectable erythropoietin activity as measured by standard techniques. Mutations at serine 104, leucine 105 and leucine 108 also significantly decreased biological activity relative to wildtype erythropoietin activity. In a similar manner, other changes at one or more of these critical sites can result in reduction of erythropoietin activity. Conversely, amino acid residues can be introduced at these critical sites to produce modified secretable human recombinant erythropoietin proteins with enhanced biological activity relative to wildtype erythropoietin activity.

Conservative substitutions can be made at one or more of the amino acid sites within residues 100–109 of the molecule. For example, alanine and aspartic acid have been used to replace arginine 103. Substitution of these amino acids by other amino acids of the same type (i.e., a positively charged, or basic, amino acid for a positively charged, or basic, one, or an acidic amino acid for an acidic one) as that present at that specific position can be made and the effect on erythropoietin's ability to regulate the growth and differentiation of red blood cell progenitors can be determined, using the methods described herein.

Substitutions at these critical sites, alone or in combination, of amino acids having characteristics different from those of amino acids whose presence at those sites has been shown to eliminate or reduce erythropoietin activity can also be made and their effect on activity assessed as described above. In particular, substitutions of some, or all, of the amino acids at one, or more, of these critical sites which result in modified secretable erythropoietin proteins with enhanced erythropoietin activity can be made. Using the techniques described herein, erythropoietin proteins having enhanced biological activity can be identified.

In addition, more radical substitutions can be made. For example, an amino acid unlike the residue present in the corresponding position in the wildtype sequence is substituted for the residue in wildtype erythropoietin (e.g., a basic amino acid is substituted for an acidic amino acid). Each resulting mutant is then evaluated using the anti-erythropoietin immunoprecipitation techniques and biological activity assays as described.

As a result, modified secretable human recombinant erythropoietin proteins having enhanced erythropoietin activity or increased heat stability can be identified. Similar techniques can be used to identify additional critical sites and subsequently, to make substitutions and evaluate their effects on erythropoietin regulating activity.

Applications of Modified Secretable Erythropoietin Proteins Having Altered Biological Activity As described above, arginine 103 is essential for erythropoietin's biological activity. Additionally, serine 104, leucine 105 and leucine 108 also appear to play a significant role in biological activity. Furthermore, these subtle point mutations do not compromise the structural integrity, (i.e., secretability) of the erythropoietin molecule. Since these described muteins have some intrinsic biological activity as detected by the assays described herein, albeit significantly reduced from wildtype erythropoietin, it is reasonable to assume that they do bind to the erythropoietin receptor. Thus, it is reasonable to assume that the mutant erythropoietin proteins will be recognized by the erythropoietin cellular receptor in essentially the same manner as the wildtype erythropoietin.

Modified secretable human recombinant erythropoietin proteins of the present invention can be used for therapy and diagnosis of various hematologic conditions. For example, an effective amount of modified secretable recombinant erythropoietin with enhanced biological activity to regulate the growth and differentiation of red blood cell progenitors can be used therapeutically (in vivo) to treat individuals who are anemic (e.g. as a result of renal disease, chemotherapy, radiation therapy, or AIDS). An effective amount of modified secretable human recombinant erythropoietin protein, as defined herein, is that amount of modified secretable erythropoietin protein sufficient to regulate growth and differentiation of red blood cell progenitor cells. For example, modified secretable erythropoietin protein with increased regulatory ability will bind to the erythropoietin receptor and stimulate the growth and differentiation of red blood cell progenitor cells. The modified secretable erythropoietin with enhanced biological activity would be more potent than the wildtype erythropoietin. Thus, to increase red blood cell growth and differentiation in anemic conditions, a lower effective dose or less frequent administration to the individual would be required.

Modified secretable erythropoietin with altered regulating activity can also be used to selectively trigger only certain events regarding the growth and differentiation of red blood cell precursors. For example, it has recently been shown that binding of erythropoietin to its receptor generates two distinct chemical signals in cells, a protein kinase C dependent activation Of the proto-oncogene c-myc and a phosphatase mediated signal to c-myb. (Spangler, R., et al., *J. Biol. Chem.* 266:681–684 (1991); Patel, H. R. and Sytkowski, A. J., Abstract 1205, *Blood* 78(10) Suppl. 1 (1991)). Thus, a modified secretable erythropoietin can be used to selectively activate either the protein kinase C or the phosphatase pathways.

An effective amount of modified secretable erythropoietin with decreased biological activity relative to wildtype erythropoietin activity, (i.e., reduced biological activity or no detectable biological activity), can be used to treat individuals with various erythroleukemias. In this case, an effective amount of modified secretable erythropoietin protein with decreased regulatory ability will bind to the erythropoietin cellular receptor. However, upon the mutant erythropoietin protein binding to the receptor, it is reasonable to predict that the mutant protein lacks ability to trigger subsequent erythropoietin events. It is further reasonable to predict that, because the mutant erythropoietin does bind to the receptor, it prevents wildtype erythropoietin from binding to the receptor (i.e., competitively inhibits the binding of wildtype erythropoietin). Thus, the red blood cell progenitors do not proliferate and/or differentiate.

The mutant erythropoietin proteins of the present invention are secretable, indicating that they retain their structural integrity, and thus fully participate in receptor recognition and binding. The initial interaction of a hormone with its cognate receptor might be expected to result in further conformational changes of the hormone ligand, thereby stabilizing the hormone/receptor complex and allowing the formation of higher ordered complexes. However, if a modified erythropoietin protein of the present invention, with no detectable erythropoietin activity, binds to its receptor, it is reasonable to assume that the subsequent events triggered by receptor binding will be altered or inhibited. Therefore, it is also reasonable to assume that growth and differentiation of red blood cell progenitor cells will be altered or inhibited, thereby inducing a remission in a red blood cell leukemia.

Recently, a constitutively active (hormone independent) form of the murine erythropoietin receptor was isolated. (Watowich, S. S., *Proc. Natl. Acad. Sci. USA* 89:2140–2144 (March 1992)). It has also been shown that the envelope glycoproteins of certain murine viruses bind to and activate the murine erythropoietin receptor. (Yoshimura, A., *Proc. Natl. Acad. Sci. USA* 87:4139–4143 (June 1990)). Thus, erythropoietin-independent activation (constitutive activation) of the erythropoietin receptor resulting in red blood cell proliferation in a mammal has been demonstrated. It is reasonable to predict that similar constitutive activation would occur in humans, (for example, a virus similar to Rauscher or Friend virus) may constitutively activate the human erythropoietin receptor also resulting in proliferation of red blood cell progenitors. A modified secretable erythropoietin, which retains its structural integrity to bind to the receptor, yet does not activate red blood cell proliferation, would be useful as an antagonist to block such constitutive activation. Moreover, modified secretable erythropoietin proteins with increased stability would provide long-acting erythropoietin antagonists.

Modified secretable erythropoietin would be useful to treat other various medical disorders. For example, polycythemia vera is characterized by uncontrollable proliferation of red blood cells and is currently treated by chemotherapy, radiation or phlebotomy. The increased number of red blood cells increases blood viscosity, leading to a hypertensive condition that can result in a stroke. It is reasonable to predict that an antagonist of erythropoietin, which binds to the receptor and blocks activation, would be a useful, non-invasive treatment.

Likewise, individuals with cyanotic heart disease often have a hyper-erythropoietin condition, leading to increased erythrocyte proliferation. Also, renal disease patients that are being treated with wildtype erythropoietin may experience an overdose. Once the wildtype erythropoietin has been administered, it continues to act. Thus, in these cases, it would be useful to administer a modified secretable erythropoietin with decreased activity to block the effects of the endogenous and exogenous erythropoietin.

Furthermore, certain hemolytic anemias, such as sickle cell anemia and thalassemia, result in rapid destruction of red blood cells. The body responds by increasing the levels of erythropoietin produced to stimulate red blood cell production. However, the red blood cells produced carry defective hemoglobin. It would be useful to use a modified secretable erythropoietin to reduce production of defective erythrocytes while another form of therapy is used to stimulate normal hemoglobin synthesis.

Erythropoietin has a relatively short plasma half-life (Spivak, J. L. and Hogans, B. B., *Blood* 73(1): 90–99 (1989); McMahon, F. G., et al., *Blood* 76(9): 1718–1722 (1990)), therefore, therapeutic plasma levels are rapidly lost, and repeated intravenous administrations must be made. Although the mechanisms responsible for this relatively short plasma half-life are not well understood, inactivation due to heat denaturation/aggregation is likely to play a role. A previously published study indicated that erythropoietin in human serum is susceptible to inactivation by heat. (Elder, G. E., et al., *Blood Cells* 11(3): 409–419 (1986)). Thus, it is reasonable to predict that modified secretable erythropoietin with increased heat stability relative to wildtype erythropoietin would have a longer plasma half-life relative to wildtype erythropoietin and thus, be useful therapeutically. This may be especially important in patients with a fever and/or an increased metabolic state.

It is also reasonable to predict that modified secretable erythropoietins with enhanced biological activity relative to wildtype erythropoietin would require a smaller quantity relative to wildtype erythropoietin to achieve a specified level of biological activity. This enhanced biological activity indicates that an effective amount of modified erythropoietin with enhanced biological activity is substantially less than a comparable effective amount of wildtype erythropoietin. The effective amount of modified erythropoietin with enhanced biological activity is defined herein as the amount of modified erythropoietin required to elicit an erythropoietin response, as indicated by increased growth and/or differentiation of erythrocytic precursor cells. Further, the effective amount of modified erythropoietin with enhanced biological activity will require less frequent administration than an equivalent amount of wildtype erythropoietin. For example, if an effective dose of erythropoietin is typically administered three times a week, modified erythropoietin with enhanced biological activity will only need to be administered once a week. Thus, a reduced quantity of modified secretable erythropoietin with enhanced biological activity would be necessary over the course of treatment than would be necessary if wildtype erythropoietin were used.

Modified secretable erythropoietin may be administered to individuals parenterally or orally. The modified secretable erythropoietin proteins of this invention can be employed in admixture with conventional pharmaceutically acceptable carriers. Suitable pharmaceutical carriers include, but are not limited to, water, salt solutions and other physiologically compatible solutions. The modified secretable erythropoietin proteins of the present invention may be administered alone, or combined with other therapeutic agents.

It will be appreciated that the amount of modified secretable erythropoietin administered to an individual in a specific case will vary according to the specific modified secretable erythropoietin protein being utilized, the particular compositions formulated, and the mode of application. Dosages for a given individual can be determined using conventional considerations such as the severity of the condition, body weight, age and overall health of the individual.

Modified secretable erythropoietin can also be used for diagnostic purposes. For example, it can be used in assay procedures for detecting the presence and determining the quantity, if desired, of erythropoietin receptor. A modified secretable erythropoietin with enhanced activity would be useful to increase the sensitivity and decrease the incubation times of such assays. It can also be used in in vitro binding assays to determine the effect of new drugs on the binding of erythropoietin protein to its receptor.

Modified secretable erythropoietin proteins described herein also provide useful research reagents to further elucidate the role of erythropoietin in erythropoiesis, as well as the structure/function relationship of erythropoietin and its cellular receptor. For example, modified secretable erythropoietin proteins may be useful for evaluating a substance for ability to regulate growth and differentiation of red blood cell progenitor cells. A reasonable indication of the ability of a substance to regulate growth and differentiation of red blood cell progenitor cells is the extent of binding of the substance to the erythropoietin receptor. The term, extent of binding, as used herein, is defined to mean the amount of substance bound to the receptor (e.g., the percent of substance bound to the receptor as compared to a control substance that binds at approximately 100 percent, or alternately, the specific activity of the test substance). A method for evaluating a substance for ability to regulate growth and differentiation of red blood cell progenitor cells can comprise comparing the extent of binding to the erythropoietin receptor of the substance to be evaluated with the extent of binding to the erythropoietin receptor of a modified secretable mutant erythropoietin protein. If the extent of binding to the erythropoietin receptor of the test substance (i.e., the substance to be evaluated) is comparable to the extent of binding to the erythropoietin receptor of the modified secretable mutant erythropoietin protein, then the extent of binding of the test substance is an indication that the ability of the substance to regulate growth and differentiation of red blood cell progenitor cells is of approximately the same ability as the modified secretable mutant erythropoietin. For example, if the specific activity of a test peptide is 25.0%, it is reasonable to assume that the test peptide has the ability to regulate growth and differentiation of red blood cell progenitor cell comparable to the R103K modified erythropoietin.

The term substance, as used herein, is defined to include proteins, e.g., analogues of wildtype erythropoietin, erythropoietin protein fragments, other proteins or peptides, and drugs.

The extent of binding to the erythropoietin receptor can be determined by using any of a number of methods familiar to those of skill in the art. For example, methods such as those described in Yonekura, S. et al., *Proc. Natl. Acad. Sci. USA* 88:1–5 (1991); Chern, Y. et al., *Blood* 76(11):2204–2209 (1990); and Krystal, G., *Exp. Hematol.* 11:649–660 (1983), the teachings of which are incorporated herein by reference, may be used.

This invention will now be illustrated by the following Examples, which are not intended to be limiting in any way.

EXAMPLE 1

Oligonucleotide-Directed Mutagenesis of Human Recombinant Erythropoietin

The oligonucleotide-directed mutagenesis used to prepare the modified secretable human recombinant erythropoietin proteins of the present invention was performed using the Altered Sites™ In Vitro Mutagenesis System (Promega Corporation of Madison, Wis.). The Altered Sites™ system consists of a unique mutagenesis vector and a simple, straightforward procedure for selection of oligonucleotide-directed mutants. The system is based on the use of a second mutagenic oligonucleotide to confer antibiotic resistance to the mutant DNA strand. The system employs a phagemid vector, pSELECT™-1, which contains two genes for antibiotic resistance. One of these genes, for tetracycline resistance, is always functional. The other, for ampicillin resistance, has been inactivated. An oligonucleotide is provided which restores ampicillin resistance to the mutant strand during the mutagenesis reaction. This oligonucleotide is annealed to the single-stranded DNA (ssDNA) template at the same time as the mutagenic oligonucleotide and subsequent synthesis and ligation of the mutant strand links the two. The DNA is transformed into a repair minus strain *E. coli*, or other suitable host, and the cells are grown in the presence of ampicillin, yielding large numbers of colonies. A second round of transformation in JM109, or a similar host, ensures proper segregation of mutant and wild type plasmids and results in a high proportion of mutants.

The pSELECT-1 plasmid is a phagemid, defined as a chimeric plasmid containing the origin of a single-stranded DNA bacteriophage. This phagemid produces ssDNA upon infection of the host cells with the helper phage R408 or M13KO7. The vector contains a multiple cloning site flanked by the SP6 and T7 RNA polymerase promoters and inserted into the lacZ α-peptide. Cloning of a DNA insert into the multiple cloning site results in inactivation of the α-peptide. When plated on indicator plates, colonies containing recombinant plasmids are white in a background of blue colonies. The SP6 and T7 promoters may be used to generate high specific activity RNA probes from either strand of the insert DNA. These sites also serve as convenient priming sites for sequencing of the insert. The pSELECT-1 vector carriers gene sequences for both ampicillin and tetracycline resistance. However, the plasmid is ampicillin sensitive because a frameshift was introduced into this resistance gene by removing the Pst I site. Therefore, propagation of the plasmid and recombinants is performed under tetracycline selection.

The pSELECT-Control vector provides a convenient white/blue positive control for mutagenesis reactions. This vector was derived from the pSELECT-1 vector by removing the Pst I site within the polylinker. The resultant frameshift in the lac α-peptide inactivated β-galactosidase and led to a white colony phenotype on indicator plates. A lacZ repair oligonucleotide (supplied with the system) may be used to introduce a four base insertion which corrects the defect in the lacZ gene and restores colony color to blue. The fraction of blue colonies obtained is an indication of the mutagenesis efficiency. When the lacZ repair oligonucleotide is used in combination with the ampicillin repair oligonucleotide to correct this defect, 80–90% of the ampicillin resistant colonies are blue. When the lacZ repair oligonucleotide is used alone, a mutagenesis efficiency of only 2–5% is seen.

The mutagenic oligonucleotide must be complementary to the single-stranded target DNA. The ssDNA produced by the pSELECT-1 phagemid is complementary to the lacZ coding strand.

The stability of the complex between the oligonucleotide and the template is determined by the base composition of the oligonucleotide and the conditions under which it is annealed. In general, a 17–20 base oligonucleotide with the mismatch located in the center will be sufficient for single base mutations. This gives 8–10 perfectly matched nucleotides on either side of the mismatch. For mutations involving two or more mismatches, oligonucleotides of 25 bases or longer are needed to allow for 12–15 perfectly matched nucleotides on either side of the mismatch.

Routinely, oligonucleotides can be annealed by heating to 70° C. for 5 minutes followed by slow cooling to room temperature.

DNA to be mutated is cloned into the pSELECT-1 vector using the multiple cloning sites. The vector DNA is then transformed into competent cells of JM109, or a similar host, and recombinant colonies are selected by plating on LB plates containing 15 µg/ml tetracycline, 0.5 mM IPTG, and 40 µg/ml X-Gal. After incubation for 24 hours at 37° C., colonies containing recombinant plasmids will appear white in a background of blue colonies.

To produce single-stranded template for the mutagenesis reaction, individual colonies containing pSELECT-Control or recombinant pSELECT-1 phagemids are grown and the cultures are infected with helper phage as described below. The single-stranded DNA produced is complementary to the lacZ coding strand and complementary to the strand of the multiple cloning site. Two helper phages R408 and M13KO 7 can be used to provide the greatest latitude in optimizing ssDNA yields.

PROTOCOL

1. Prepare an overnight culture of cells containing pSELECT™-1 or pSELECT™-Control phagemid DNA by picking individual tetracycline resistant colonies from a fresh plate. Inoculate 1–2 ml of TYP broth (Promega) containing 15 µg/ml tetracycline and shake at 37° C.

2. The next morning inoculate 5 ml of TYP broth containing 15 µg/ml tetracycline with 100 µl of the overnight culture. Shake vigorously at 37° C. for 30 minutes in a 50 ml tube.

3. Infect the culture with helper phage R408 or M13KO7 at an m.o.i. (multiplicity of infection) of 10 (i.e., add 10 helper phage particles per cell). For the helper phages supplied with this system, add 40 µl. Continue shaking for 6 hours to overnight with vigorous agitation.

4. Harvest the culture supernatant by pelleting the cells at 12,000 x g for 15 minutes. Pour the supernatant into a fresh tube and spin again for 15 minutes.

5. Precipitate the phage by adding 0.25 volume of phage precipitation solution (Promega) to the supernatant. Leave on ice for 30 minutes, then centrifuge for 15 minutes at 12,000 x g. Thoroughly drain the supernatant.

6. Resuspend the pellet in 400 µl of TE buffer (Promega) and transfer the sample to a microcentrifuge tube.

7. Add 0.4 ml of chloroform:isoamyl alcohol (24:1) to lyse the phage, vortex for 1 full minute, and centrifuge in a microcentrifuge (12,000 x g) for 5 minutes. This step removes excess PEG.

8. Transfer the upper, aqueous phase (containing phagemid DNA) to a fresh tube, leaving the interface behind. Add 0.4 ml of TE-saturated phenol:chloroform to the aqueous phase, vortex for 1 full minute, and centrifuge as in step 7.

9. Transfer the upper, aqueous phase to a fresh tube and repeat the phenol extraction as in step 8. If necessary, repeat this extraction several times until there is no visible material at the interface.

10. Transfer the upper, aqueous phase to a fresh tube and add 0.5 volume (200 µl) of 7.5M ammonium acetate plus 2 volumes (1.2 ml) of ethanol. Mix and leave at −20° C. for 30 minutes to precipitate the phagemid DNA.

11. Centrifuge at 12,000 x g for 5 minutes, remove the supernatant, carefully rinse the pellet with 70% ethanol, and centrifuge again for 2 minutes. Drain the tube and dry the pellet under vacuum. The pellet may be difficult to see.

12. Resuspend the DNA in 20 µl of $H_2O$. The amount of DNA present can be estimated by agarose gel electrophoresis of a 2 µl sample.

The mutagenesis reaction involves annealing of the ampicillin repair oligonucleotide and the mutagenic oligonucleotide to the ssDNA template, followed by the synthesis of the mutant strand with T4 DNA polymerase. The heteroduplex DNA is then transformed into the repair minus *E. coli* strain DMH71-18 mutS or other suitable strain. Mutants are selected by overnight growth in the presence of ampicillin. Plasmid DNA is the isolated and transformed into the JM109 strain, or other suitable strain. Mutant, ampicillin resistant colonies may be screened by direct sequencing of the plasmid DNA.

A. Annealing Reaction and Mutant Strand Synthesis

The amount of oligonucleotide required in this reaction may vary depending on the size and amount of the single-stranded DNA template. The ampicillin repair oligonucleotide (27 bases long) should be used at a 5:1 oligo:template ratio and the mutagenic oligonucleotide should be used at a 25:1 oligo:template ratio. A typical reaction may contain approximately 100 ng (0.05 pmol) of ssDNA.

PROTOCOL

1. Prepare the mutagenesis or control annealing reactions as described below.

| Mutagenesis Annealing Reaction | |
|---|---|
| Recombinant pSELECT ™-1 ssDNA | 0.05 pmol |
| Ampicillin repair oligonucleotide (2.2 ng/µl) | 1µ (0.25 pmol) |
| Mutagenic oligonucleotide, phosphorylated (see Table 1) | 1.25 pmol |
| 10X Annealing buffer | 2 µl |
| Sterile H$_2$O | to final volume 20 µl |

| Control Annealing Reaction | |
|---|---|
| pSELECT ™-Control ssDNA | 100 ng (0.05 pmol) |
| Ampicillin repair oligonucleotide (2.2 ng/µl) | 1 µl (0.25 pmol) |
| lacZ control oligonucleotide (10.8 ng/gl) | 1 µl (1.25 pmol) |
| 10X Annealing buffer | 2 µl |
| Sterile H$_2$O | to final volume 20 µl |

2. Heat the annealing reaction to 70° C. for 5 minutes and allow it to cool slowly to room temperature (15–20 minutes).

3. Place the annealing reaction on ice and add the following:

| 10X Synthesis buffer | 3 µl |
|---|---|
| T4 DNA polymerase (10 u/µl) | 1 µl |
| T4 DNA ligase (2 u/µl) | 1 µl |
| Sterile H$_2$O | 5 µl |
| | to final volume 20 µl |

4. Incubate the reaction at 37° C. for 90 minutes to perform mutant strand synthesis and ligation.

| Primer Length | ng of Primer Equal to 1.25 pmol |
|---|---|
| 17 mer | 7.0 ng |
| 20 mer | 8.3 ng |
| 23 mer | 9.5 ng |
| 26 mer | 10.8 ng |
| 29 mer | 12.0 ng |

B. Transformation into BMH 71-18 mutS

PROTOCOL

1. Add 3 µl of DMSO to 200 µl of BMH71-18 mut S competent cells, mix briefly, and then add the entire synthesis reaction from step A.4.

2. Let the cells sit on ice for 30 minutes. 3. OPTIONAL: For some strains, a heat shock at 42° C. for 1–2 minutes after the incubation on ice has been reported to increase transformation efficiency. In our experience, however, a heat shock does not significantly affect the efficiency of transforming BMH71-18 mut S.

4. Add 4 ml of LB medium and incubate at 37° C. for 1 hour to allow the cells to recover.

5. Add ampicillin to a final concentration of 125 µg/ml and incubate at 37° C. for 12–14 hours with shaking.

NOTE: As a control to check the synthesis reaction, 1 ml of the culture can be removed after the one hour recovery step, spun down, resuspended in 50 µl of LB medium, and plated on LB plates (pg. 12) containing 125 µg/ml ampicillin. This is a check for the presence of ampicillin resistant transformants; a second round of transformation is necessary before screening for mutants.

C. Plasmid Mini-Prep Procedure

This procedure is used to isolate pSELECT-1 or pSELECT-Control plasmid DNA from the overnight culture of BMH 71-18 mut S (step B.5, above). A yield of 1–3 µg of plasmid DNA may be expected.

PROTOCOL

1. Place 1.5 ml of the overnight culture into a microcentrifuge tube and centrifuge at 12,000 x g for 1 minute. The remainder of the overnight culture can be stored at 4° C.

2. Remove the medium by aspiration, leaving the bacterial pellet as dry as possible.

3. Resuspend the pellet by vortexing in 100 µl of ice-cold miniprep lysis buffer (Promega).

4. Incubate for 5 minutes at room temperature.

5. Add 200 µl of a freshly prepared solution containing 0.2N NaOH, 1% SDS. Mix by inversion. DO NOT VORTEX. Incubate for 5 minutes on ice.

6. Add 150 µl of ice-cold potassium acetate solution, pH 4.8 (Promega). Mix by inversion or gentle vortexing for 10 seconds. Incubate for 5 minutes on ice.

7. Centrifuge at 12,000 x g for 5 minutes.

8. Transfer the supernatant to a fresh tube, avoiding the white precipitate.

9. Add 1 volume of TE-saturated phenol/chloroform (Promega). Vortex for 1 minute and centrifuge at 12,000 x g for 5 minutes.

10. Transfer the upper, aqueous phase to a fresh tube and add 1 volume of chloroform:isoamyl alcohol)24:1). Vortex for 1 minute and centrifuge as in step 9.

11. Transfer the upper, aqueous phase to a fresh tube and add 2.5 volumes of 100% ethanol. Mix and allow to precipitate 5 minutes on dry ice.

12. Centrifuge at 12,000 x g for 5 minutes. Rinse the pellet with 70% ethanol (prechilled) and dry the pellet under vacuum.

13. Dissolve the pellet in 50 µl of sterile deionized water. Add 0.5 µl of 100 µg/ml DNase-free RNase A (Promega) and incubate for 5 minutes at room temperature.

14. The yield of plasmid DNA can be determined by electrophoresis on an agarose gel.

D. Transformation into JM109 Host Cells

PROTOCOL

1. Add 3 µl of DMSO to 200 µl of JM109 competent cells, mix briefly, and add 0.05–0.10 µg of plasmid DNA from step C.14. Other suitable host cells may be used.

2. Let the cells sit on ice for 30 minutes.

3. OPTIONAL: A heat shock may be performed at this step.

4. Add 2 ml of LB medium and incubate at 37° C. for 1 hour to allow the cells to recover.

5. Divide the culture into two microcentrifuge tubes and spin for 1 minute in a microcentrifuge.

6. Pour off the supernatant and resuspended the cells in each tube in 50 µl of LB medium.

7. Plate the cells in each tube on an LB plate containing 125 µg/ml ampicillin and incubate at 37° C. for 12–14 hours.

E. Analysis of Transformants

The Altered Sites mutagenesis procedure generally produces greater than 50% mutants, so colonies may be screened by direct sequencing. A good strategy is to pick 10 colonies and start by sequencing 4 of these. If the mutation is located within 200–300 bases of either end of the DNA

EXAMPLE 2

Cell Culture and Transfection

COS-7 cells were obtained from the American Type Culture Collection (Rockville, Md.) and maintained in Dulbecco's modified Eagle's medium containing 10% fetal bovine serum (GIBCO). Transient expression of cDNAs was performed using a DEAE-Dextran protocol modified by 0.1 mM chloroquine treatment (Sussman, D. J. & Milman, *Mol. Cell Biol.* 4:1641–1645 (1984); Ausubel, F. M., et al., "Current Protocols in Molecular Biology" pp.921–926, John Wiley and Son, New York, (1989)). 3 days before the transfection, COS-7 cells were plated at $2\times10^5$/10-cm tissue culture dish. 4 µg DNA were used in each transfection. Medium was collected 3 days after transfection and assayed for erythropoietin activity and protein.

EXAMPLE 3

Immunoprecipitation of Erythropoietin

Wildtype and mutant erythropoietin contained in supernatant medium from COS cell transfections were diluted one- to four-fold with Dulbecco's modified Eagle medium containing 10% fetal bovine serum. After one hour incubation at 37 degrees C. with a monoclonal anti-peptide antibody to erythropoietin directed against amino acids 1–26 or 99–129, an equal volume of Omnisorb (Calbiochem) was added to the samples and the suspension was incubated for one hour at 4 degrees C. The Omnisorb was pelleted by centrifugation at 4000 rpm for 30 seconds. The erythropoietin remaining in the supernatant which was not bound by the monoclonal antibody was measured by radioimmunoassay. The amount of erythropoietin bound by antibody (as a percent) was calculated by subtracting the amount in the supernatant from 100%, the starting concentration.

Equivalents

Those skilled in the art will recognize, or be able to ascertain, using no more than routine experimentation, many equivalents to the specific embodiments of the invention described specifically herein. such equivalents are intended to be encompassed in the scope of the following claims.

---

The invention claimed is:

1. A mutant human erythropoietin protein having an amino acid sequence which differs from the sequence of wild-type human erythropoietin at the position corresponding to glycine$^{101}$ of said wild-type erythropoietin, wherein said mutant protein has increased biological activity relative to wild-type human erythropoietin as determined in an in vitro erythropoietic bioassay.

2. A mutant erythropoietin protein according to claim 1, wherein the amino acid residue at the position corresponding to glycine$^{101}$ of wild-type erythropoietin is alanine.

3. -human erythropoietin.

4. A nucleic acid molecule encoding a mutant human erythropoietin protein according to claim 1.

5. A nucleic acid molecule encoding a mutant human erythropoietin protein according to claim 2.

6. A nucleic acid molecule encoding -human erythropoietin according to claim 3.

7. A pharmaceutical composition comprising a mutant human erythropoietin protein according to claim 1 and a pharmaceutically acceptable carrier.

8. A pharmaceutical composition comprising a mutant human erythropoietin protein according to claim 2 and a pharmaceutically acceptable carrier.

9. A pharmaceutical composition comprising -human erythropoietin according to claim 3 and a pharmaceutically acceptable carrier.

10. A method of promoting the growth and differentiation of red blood cell progenitors in an individual, comprising the step of administering a mutant human erythropoietin protein according to claim 1 to said individual.

11. A method of promoting the growth and differentiation of red blood cell progenitors in an individual, comprising the step of administering a mutant human erythropoietin protein according to claim 2 to said individual.

12. A method of promoting the growth and differentiation of red blood cell progenitors in an individual, comprising the step of administering -human erythropoietin according to claim 3 to said individual.

13. A mutant human erythropoietin protein having an amino acid sequence which differs from the sequence of wild-type human erythropoietin at the position corresponding to arginine$^{103}$ of said wild-type erythropoietin, wherein said mutant protein has decreased biological activity relative to wild-type human erythropoietin as determined in an in vitro erythropoietic bioassay, and wherein a recombinant host cell producing a polypeptide having the amino acid sequence of said mutant protein is capable of secreting said polypeptide.

14. A mutant erythropoietin protein according to claim 13, wherein said mutant protein has increased heat stability relative to wild-type erythropoietin.

15. A mutant erythropoietin protein according to claim 13, wherein the amino acid residue at the position corresponding to arginine$^{103}$ of wild-type erythropoietin is aspartate.

16. -human erythropoietin.

17. A nucleic acid molecule encoding a mutant human erythropoietin protein according to claim 13.

18. A nucleic acid molecule encoding a mutant human erythropoietin protein according to claim 14.

19. A nucleic acid molecule encoding a mutant human erythropoietin protein according to claim 15.

20. A nucleic acid molecule encoding -human erythropoietin according to claim 16.

21. A pharmaceutical composition comprising a mutant human erythropoietin protein according to claim 13 and a pharmaceutically acceptable carrier.

22. A pharmaceutical composition comprising a mutant human erythropoietin protein according to claim 14 and a pharmaceutically acceptable carrier.

23. A pharmaceutical composition comprising a mutant human erythropoietin protein according to claim 15 and a pharmaceutically acceptable carrier.

24. A pharmaceutical composition comprising -human erythropoietin according to claim 16 and a pharmaceutically acceptable carrier.

25. A method of inhibiting the growth and differentiation of red blood cell progenitors in an individual, comprising the step of administering a mutant human erythropoietin protein according to claim 13 to said individual.

26. A method of inhibiting the growth and differentiation of red blood cell progenitors in an individual, comprising the step of administering a mutant human erythropoietin protein according to claim 14 to said individual.

27. A method of inhibiting the growth and differentiation of red blood cell progenitors in an individual, comprising the step of administering a mutant human erythropoietin protein according to claim 15 is to said individual.

28. A method of inhibiting the growth and differentiation of red blood cell progenitors in an individual, comprising the step of administering -human erythropoietin according to claim 16 to said individual.

* * * * *

UNITED STATES PATENT AND TRADEMARK OFFICE
CERTIFICATE OF CORRECTION

PATENT NO. : 5,614,184
DATED : March 25, 1997
INVENTOR(S) : Arthur J. Sytkowski and Jennifer Grodberg It is certified that error appears in the above-indentified patent and that said Letters Patent is hereby corrected as shown below:

```
Claim 3,  line 58:   before the "-", insert --[Alanine¹⁰¹]--.
Claim 6,  line 63:   before the "-", insert --[Alanine¹⁰¹]--.
Claim 9,  line 51:   before the "-", insert --[Alanine¹⁰¹]--.
Claim 12, line 64:   before the "-", insert --[Alanine¹⁰¹]--.
Claim 16, line 16:   before the "-", insert --[Aspartate¹⁰³]--.
Claim 20, line 23:   before the "-", insert --[Aspartate¹⁰³]--.
Claim 24, line 7:    before the "-", insert --[Aspartate¹⁰³]--.
Claim 27, line 21:   delete "is".
Claim 28, line 24:   before the "-", insert --[Aspartate¹⁰³]--.
```

Signed and Sealed this

Second Day of September, 1997

*Attest:*

BRUCE LEHMAN

*Attesting Officer*   Commissioner of Patents and Trademarks